United States Patent
Bérubé

(10) Patent No.: US 7,153,844 B2
(45) Date of Patent: Dec. 26, 2006

(54) ESTROGEN-LINKED PLATINUM (II) COMPLEXES AS ANTICANCER AGENTS

(75) Inventor: Gervais Bérubé, 5330, J.H. Fortier, Trois-Rivières, Québec (CA) G8Y 4Z4

(73) Assignee: Gervais Berube, Trois-Riviere (CA)

( * ) Notice: Subject to any disclaimer, the term of this patent is extended or adjusted under 35 U.S.C. 154(b) by 268 days.

(21) Appl. No.: 10/397,332

(22) Filed: Mar. 27, 2003

(65) Prior Publication Data

US 2004/0006051 A1 Jan. 8, 2004

Related U.S. Application Data

(60) Provisional application No. 60/367,752, filed on Mar. 28, 2002.

(51) Int. Cl.
*A61K 31/58* (2006.01)
*C07J 43/00* (2006.01)

(52) U.S. Cl. ............... 514/176; 540/107; 540/109; 540/112

(58) Field of Classification Search ............... 514/176; 540/107, 109, 112
See application file for complete search history.

(56) References Cited

OTHER PUBLICATIONS

E. Wong and C.M. Giandomenico << Current Status of Platinum-Based Antitumor Drugs >>, Chemical Review, 99, 2451-2466 (1999).
E.R. Jamieson and S.J. Lippard, << Structure, Recognition, and Processing of Cisplatin-DNA Adducts >> Chemical Review, 99 2499-2510 (1999).
J. Reedijk, <<Why Does Cisplatin Reach Guanine-N7 with Competing S-Donor Ligands Available in the Cell?>>, Chemical Review, 99, 2499-2510 (1999).
Tremblay, R. , S. Auge rand D. Poirier *Synthetic Communications*, 25, 2483-2495 (1995).
Tedesco, R., R. Fiaschi and E. Napolitano *Synthesis*, 12, 1493-1495 (1995).
W..C. Still, M. Kahn and A. Mitra, J. Org. Chem., 43, 2923 (1978).
Y. He, S. Groleau, R.C.-Gaudreault, M. Caron, H.-H. Thérien, G. Bérubé, Bioorganic & Medicinal Chemistry Letters, 19, 2217-2222 (1995).
J. Charmichael et al. (Cancer Res. 47, 943-946 (1987).
C.H.J. Ford et al., Cancer Chemother. Pharmacol. 24, 295-301 (1986).
Alley, M. C. et al (Cancer Research. No. 46, 589-601, 1987.
Boyd, M.R. & Paull, K.D. (Drug Development Research. 34, 91-109, (1995)).

*Primary Examiner*—Barbara P. Badio
(74) *Attorney, Agent, or Firm*—Ogilvy Renault LLP

(57) ABSTRACT

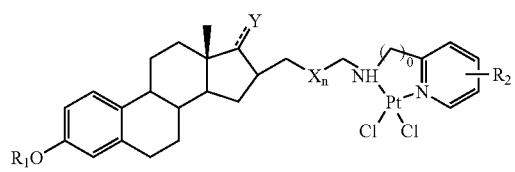

wherein X may be —$CH_2$—O—$CH_2$— or —$CH_2$—, wherein n may be 1, 2, 3, 4 or 5 when X is —$CH_2$—O—$CH_2$—, wherein n may be 2, 3, 4, 5, 6, 7, 8, 9 or 10 when X is —$CH_2$—, wherein o may be 1, 2 or 3, wherein Y may be O or 17β-OH, where the dotted line represents the presence or absence of a second chemical bond,
wherein $R_1$ may be selected from the group consisting of H, straight alkyl groups of 1 to 5 carbon atoms, and branched alkyl groups of 3 to 5 carbon atoms,
wherein $R_2$ may be selected for the group consisting of H, straight alkyl groups of 1 to 4 carbon atoms, branched alkyl groups of 3 or 4 carbon atoms, F, Cl, Br, I, —$CF_3$, —$NO_2$, —$OR_1$, where $R_1$ is as defined hereinabove, —$COR_1$, where $R_1$ is as defined hereinabove, and —$CH_2OH$.
These compounds possess anticancer activity against hormono-dependent breast, uterus as well as ovarian cancers.

29 Claims, No Drawings

ESTROGEN-LINKED PLATINUM (II) COMPLEXES AS ANTICANCER AGENTS

This application claims benefit of U.S. Provisional Application No. 60/367,752 filed Mar. 28, 2002.

TECHNICAL FIELD OF THE INVENTION

This invention concerns a novel class of estrogen-linked platinum (II) (E-Pt(II)) complexes possessing potent in vitro cytotoxic activity. It describes the synthetic methodology to make these platinum (II) derivatives from readily available estrone analogues and their biological applications. In addition, this invention relates to different pharmaceutical compositions comprising these compounds. The compounds and the pharmaceutical composition of this invention have been shown to possess potent in vitro cytotoxic activity on human breast and uterus cancer. The cytotoxic activity of these compounds may be advantageously used to provide compounds with anticancer activity against hormono-dependent breast, uterus as well as ovarian cancers.

BACKGROUND OF THE INVENTION

Several platinum coordination complexes such as cis-diamminedichloroplatinum (II) (cisplatin) and diamine[1,1-cyclobutanedicarboxylato]-O,O'-platinum (II) (carboplatin) are currently used in chemotherapy of neoplastic diseases. These complexes of a non-essential heavy metal, exhibit a remarkable antitumor effectiveness and a broad spectrum of activity. It is widely believed that the antitumor activity of platinum drugs is a consequence of their interaction with DNA. Cisplatin binds readily to guanine residues of DNA molecules. Cisplatin has proved very successful in the treatment of a variety of human solid tumors such as genitourinary and gynecologic tumors as well as head, neck and lung tumors. Unfortunately, the development of cellular resistance to cisplatin in mammalian cells is common and is believed to occurs via, four main mechanisms: (a) increased efficiency of repair of platinum-DNA lesions, (b) increased inactivation of drug by elevated levels of cellular low-molecular weight thiols, particularly glutathione, (c) metallothionein, and (d) decreased cellular uptake of drug. Its toxic effects, particularly kidney toxicity and neurotoxicity, also limit the clinical utility of the drug. It is noteworthy that carboplatin is less toxic than cisplatin and can be given at a much higher dose (up to 2000 mg/dose for carboplatin as compare to a typical dose of 100 mg/day for cisplatin).

More recently, two other platinum (II) derivatives were approved for use in some countries. (trans-L-diaminocyclohexane)oxalatoplatinum(II) (oxaliplatin (4)) has been approved for the secondary treatment of metastatic colorectal cancer in France and other European countries. cis-diammine-glycoloato-O,O'-platinum (II) (nedaplatin (5)) has received approval for use in Japan. Unfortunately, oxaplatin and nedaplatin have not shown any distinct advantages over cisplatin and carboplatin. The search for platinum complexes with a broader spectrum of activity, less toxicity, improved clinical effectiveness against tumors characterized by intrinsic or acquired resistance to cisplatin is ongoing.

Scheme 1: Structure of the known platinum (II) complexes.

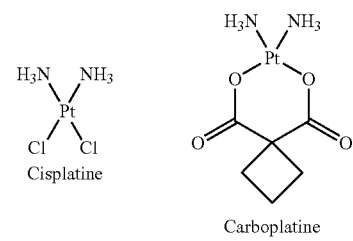
Cisplatine

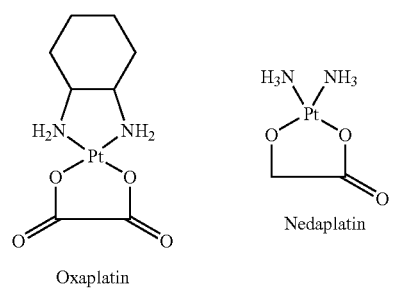
Carboplatine

Oxaplatin

Nedaplatin

The following literature reviews present a broad overview of the actual knowledge of platinum-based antitumor agents as well as of their mechanism of action:

E, Wong and C. M. Giandomenico, << Current Status of Platinum-Based Antitumor Drugs >>, Chemical Review, 99, 2451–2466 (1999)

E. R. Jamieson and S. J. Lippard, << Structure, Recognition, and Processing of Cisplatin-DNA Adducts >>. Chemical Review, 99, 2467–2498 (1999)

J. Reedijk, << Why Does Cisplatin Reach Guanine-N7 with Competing S-Donor Ligands Available in the Cell?>>, Chemical Review, 99, 2499–2510 (1999)

SUMMARY OF THE INVENTION

The present invention provides a novel class of estrogen-linked platinum (II) molecules including their pharmaceutically acceptable derivatives. These molecules possess potent in vitro cytotoxic activity on human breast and uterus cancers. Therefore, these compounds may be advantageously used to provide compounds with anticancer activity against hormono-dependent breast, uterus as well as ovarian cancers. These compounds can be used alone or in combination with other therapeutic or prophylactic agents for the treatment of breast, uterus and ovarian cancers.

It is the main objective of this invention to provide a novel class of molecules that are anticancer agents. The present invention relates to a class of estrogen-platinum (II) complexes linked at carbon 16 of the steroid nucleus (see estradiol ($E_2$) molecule below) as well as their pharmaceutically acceptable derivatives. This invention further provides an efficient methodology to bind a variety of side chain at position 16 of the steroid nucleus that could be further transformed into novel platinum (II) complexes.

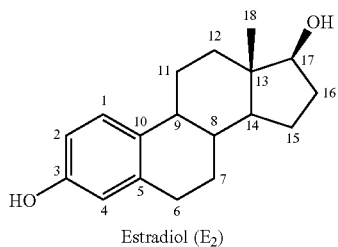

Estradiol (E$_2$)

Accordingly, the present invention in accordance with one aspect thereof provides a compound(s) of formula I

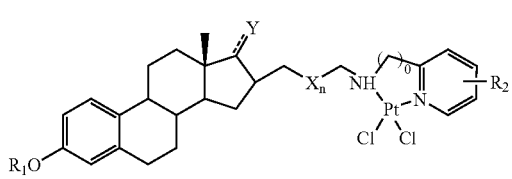

I wherein X may be —CH$_2$—O—CH$_2$— or —CH$_2$—, wherein n may be 1, 2, 3, 4 or 5 when X is —CH$_2$—O—CH$_2$—, wherein n may be 2, 3, 4, 5, 6, 7, 8, 9 or 10 when X is —CH$_2$—, wherein o may be 1, 2 or 3, wherein Y may be O or 17β-OH, the dotted line representing the presence or absence of a second chemical bond, wherein R$_1$ may be selected from the group consisting of H, straight alkyl groups of 1 to 5 carbon atoms, and branched alkyl groups of 3 to 5 carbon atoms, wherein R$_2$ may be selected for the group consisting of H, straight alkyl groups of 1 to 4 carbon atoms, branched alkyl groups of 3 or 4 carbon atoms, F, Cl, Br, I, —CF$_3$, —NO$_2$, —OR$_1$, where R$_1$ is as defined hereinabove, —COR$_1$, where R$_1$ is as defined hereinabove, and —CH$_2$OH.

In a further aspect, the present invention provides, a compound(s) of formula IA

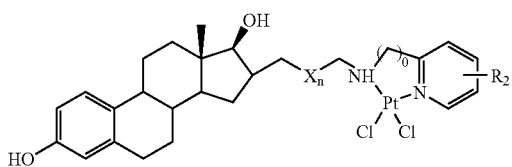

IA wherein X may be —CH$_2$—O—CH$_2$— or —CH$_2$—, wherein n may be 1, 2, 3, 4 or 5 when X is —CH$_2$—O—CH$_2$—, wherein n may be 2, 3, 4, 5, 6, 7, 8, 9 or 10 when X is —CH$_2$—, wherein o may be 1, 2 or 3, wherein R$_2$ may be selected for the group consisting of H, straight alkyl groups of 1 to 4 carbon atoms, and branched alkyl groups of 3 or 4 carbon atoms, F, Cl, Br, I, —CF$_3$, —NO$_2$, —OR$_1$, —COR1 and —CH$_2$OH, R$_1$ being selected from the group consisting of H, straight alkyl groups having from 1 to 5 carbon atoms and branched alkyl groups having from 3 to 5 carbon atoms.

In accordance with the present invention, X may be —CH$_2$— while n may be 9, o may be 1, 2 or 3 and R$_2$ may be H.

In accordance with the present invention, X may be —CH$_2$—O—CH$_2$— while n may be 3, o may be 1, 2 or 3 and R$_2$ may be H.

In yet another aspect, the present invention provides, a compound(s) of formula IB

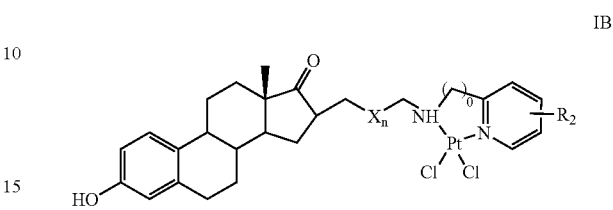

IB wherein X may be —CH$_2$—O—CH$_2$— or —CH$_2$—, wherein n may be 1, 2, 3, 4 or 5 when X is —CH$_2$—O—CH$_2$—, wherein n may be 2, 3, 4, 5, 6, 7, 8, 9 or 10 when X is —CH$_2$—, wherein o may be 1, 2 or 3, wherein R$_2$ may be selected for the group consisting of H, straight alkyl groups of 1 to 4 carbon atoms, branched alkyl groups of 3 or 4 carbon atoms, F, Cl, Br, I, —CF$_3$, —NO$_2$, —OR$_1$, —COR1 and —CH$_2$OH, R$_1$ being selected from the group consisting of H, straight alkyl groups having from 1 to 5 carbon atoms and branched alkyl groups p having from 3 to 5 carbon atoms.

In accordance with the present invention, X may be —CH$_2$— while n may be 9, o may be 1, 2 or 3 and R$_2$ may be H.

In accordance with the present invention, X may be —CH$_2$—O—CH$_2$— while n may be 3, o may be 1, 2 or 3 and R$_2$ may be H.

Accordingly, the present invention in accordance with one aspect thereof provides a compound(s) of formula II

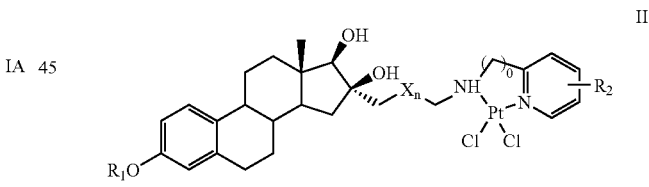

II wherein X may be —CH$_2$—O—CH$_2$— or —CH$_2$—, wherein n may be 1, 2, 3, 4 or 5 when X is —CH$_2$—O—CH$_2$—, wherein n may be 2, 3, 4, 5, 6, 7, 8, 9 or 10 when X is —CH$_2$—, wherein o may be 1, 2 or 3, wherein R$_1$ may be selected from the group consisting of H, straight alkyl groups of 1 to 5 carbon atoms, and branched alkyl groups of 3 to 5 carbon atoms, wherein R$_2$ may be selected for the group consisting of H, straight alkyl groups of 1 to 4 carbon atoms, branched alkyl groups of 3 or 4 carbon atoms, F, Cl, Br, I, —CF$_3$, —NO$_2$, —OR1, where R$_1$ is as defined hereinabove, —COR1, where R$_1$ is as defined hereinabove, and —CH$_2$OH.

In a further aspect, the present invention provides, a compound(s) of formula IIA

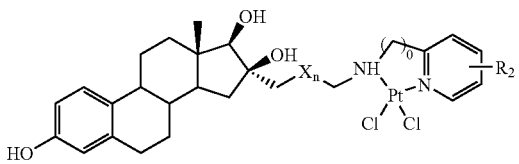

IIA wherein X may be —CH$_2$—O—CH$_2$— or —CH$_2$—, wherein u may be 1, 2, 3, 4 or 5 when X is —CH$_2$—O—CH$_2$—, wherein n may be 2, 3, 4, 5, 6, 7, 8, 9 or 10 when X is —CH$_2$—, wherein o may be 1, 2 or 3, wherein R$_2$ may be selected for the group consisting of H, straight alkyl groups of 1 to 4 carbon atoms, branched alkyl groups of 3 or 4 carbon atoms, F, Cl, Br, I, —CF$_3$, —NO$_2$, —OR$_1$, —COR$_1$ and —CH$_2$OH, R$_1$ being selected from the group consisting of H, straight alkyl groups having from 1 to 5 carbon atoms and branched alkyl groups having from 3 to 5 carbon atoms.

In accordance with the present invention, X may be —CH$_2$— while n may be 2, 4, 6 or 8, o may be 1, 2 or 3 and R$_2$ may be H.

In accordance with the present invention, X may be —CH$_2$—O—CH$_2$— while n may be 2, o may be 1, 2 or 3 and R$_2$ may be H.

This invention also provides in a further aspect, pharmaceutical compositions comprising a pharmaceutically acceptable carrier and at least one compound of formula I, IA, IB, II and IIA as defined herein. The pharmaceutical composition may comprise, for example, a pharmaceutically effective amount of such one or more compounds or pharmaceutically acceptable derivatives.

The term "pharmaceutically effective amount" refers to an amount effective in treating breast, uterus or ovarian cancer in patient. It is also to be understood herein that a "pharmaceutically effective amount" may be interpreted as an amount giving a desired therapeutic effect, either taken into one dose or in any dosage or route or taken alone or in combination with other therapeutic agents. In the case of the present invention, a "pharmaceutically effective amount" may be understood as an amount having cytotoxic effect on breast, uterus or ovarian cancers.

The compounds of this invention are easily prepared using conventional techniques from readily available and inexpensive starting materials. The detailed description of these strategies are presented in schemes 2 to 7 discussed below.

Scheme 2 illustrates the preparation of key estrone intermediates (compounds 4 to 8) needed for the synthesis of the new anticancer agents described in this invention.

As shown on scheme 2, a side chain is efficiently introduced at position 16 of estrone (1) via the alkylation of the β-cetoester 3 with various electrophiles (E$^+$). The side chains are easily linked in four chemical steps with an overall yield of 63.4% for compound 4, 71.3% for compound 5, 57% for compound 6, 84.6% for compound 7 and 75.7% for compound 8. These intermediates can be further transformed into novel platinum (II) complexes.

Note: The reaction conditions of each step are presented directly on the schemes.

Commercially available estrone (1) is initially protected either as a benzyl ether 2 (R=Bn) or as a tetrahydropyranyl ether 2 (R=THP) under standard reaction conditions (see T. W. Greene and P. G. M. Wuts, Protective groups in Organic Synthesis, 3$^{rd}$ Edition, John Wiley & Sons, Inc. 2000). Any adequate protective group could be used to protect the phenol function of estrone (1). The derivative 2 is transformed into the β-cetoester 3 upon treatment with dimethyl carbonate in the presence of a mixture of NaH/KH (see Tremblay, R., S. Auger and D. Poirier. *Synthetic Communications*, 25, 2483–2495 (1995)). Alkylation of derivative 3 with 1-tetrahydropyranyloxy-11-bromoundecane under phase transfer catalyst reaction conditions gave derivative 4 in 70% yield. As shown on scheme 2, other electrophiles can be used yielding a variety of side chains at position 16 of the estrone nucleus.

Scheme 2: Functionalization of estrone at position 16 with various side chains

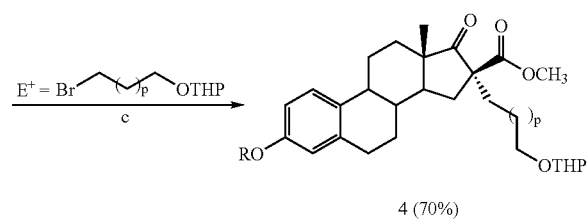

4 (70%)

5 (80%)

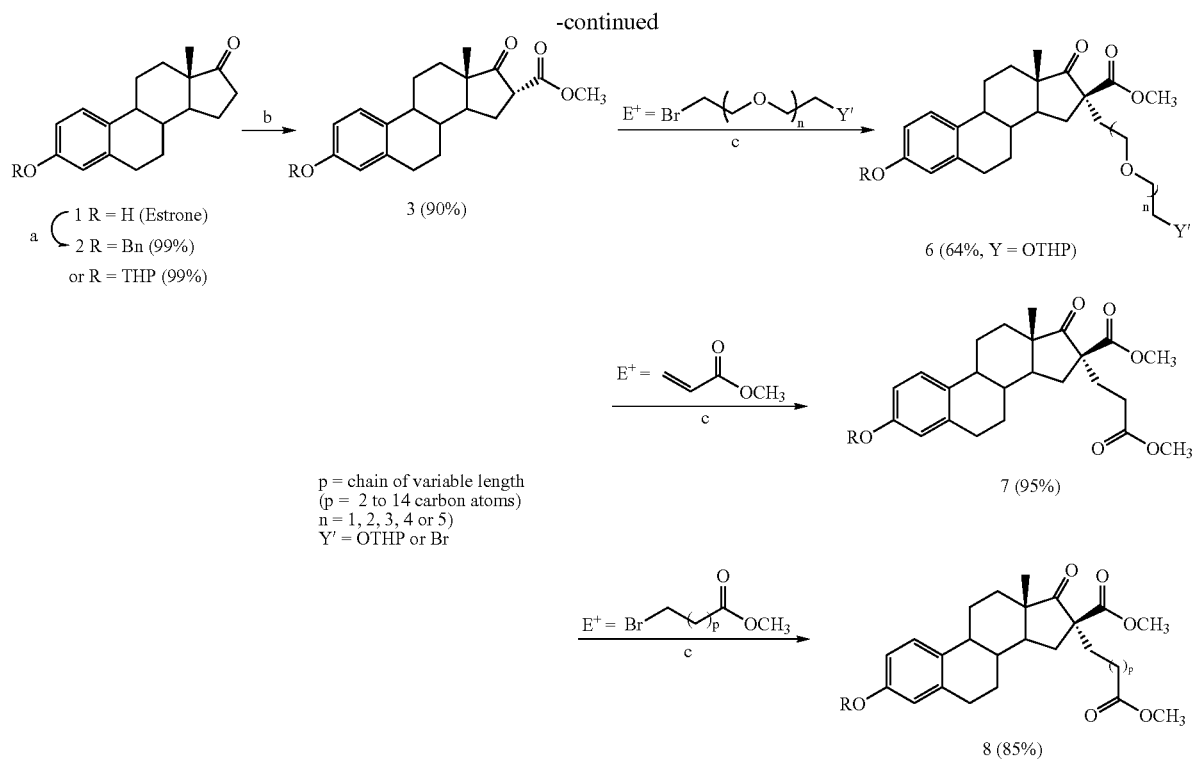

p = chain of variable length
(p = 2 to 14 carbon atoms)
n = 1, 2, 3, 4 or 5)
Y' = OTHP or Br Reagents: (a) BnBr, Bu₄N⁺HSO₄⁻, 10% aq. NaOH, CH₂Cl₂, Δ; (b) NaH, KH, Dimethyl carbonate, THF, Δ; (c) E⁺, Bu₄N⁺HSO₄⁻, 10% aq. NaOH, CH₂Cl₂, Δ.

Scheme 3 illustrates a generic example for the transformation of derivative 4 into platinum (II) complexes according to this invention.

Derivative 4 (R=Bn) was simultaneously decarboalkoxylated and deprotected upon treatment with lithium chloride in a mixture of DMF/H$_2$O at reflux to give derivative 9 in 80% yield. Reduction of the steroidal 17-ketone with lithium aluminum hydride yielded 17β-alcohol 10 with 78% yield. The primary alcohol is transformed into a bromide (64% yield) with carbon tetrabromide and triphenylphosphine in dry diethyl ether. Removal of the benzyl protective group by hydrogen gas in presence of 10% Pd/C yielded the bromodiol derivative 11 (90% yield). The overall yield for the transformation of 9 into 11 is 45%. The amine was obtained by nucleophilic displacement of the bromide with an appropriate 2-aminoalkyl pyridine (e.g., for example, 2-amimomethylpyridine (o=1) or 2-(2'-aminoethyl)pyridine (o=2)) at reflux in methanol. The resulting amine intermediate is immediately transformed without purification into a platinum (II) complex 12 (51% overall from 11) by treatment with potassium tetrachloroplatinate (II) in a mixture of DMF and H$_2$O. The synthesis of E$_2$-Pt(II) complexes 12 was done in nine chemical steps with an overall yield of 11.5%. This strategy can be used to yield a large variety of novel E$_2$-Pt (II) complexes by using other aminoalkyl pyridines. It is also possible to synthesized estrone platinum (II) complexes (E$_1$-Pt (II)) from derivative 9, if the 17-ketone is not reduced at all, but is transformed into the bromide following the strategy of scheme 3.

Scheme 3: Synthesis of E$_2$-Pt (II) complexes from derivative 4

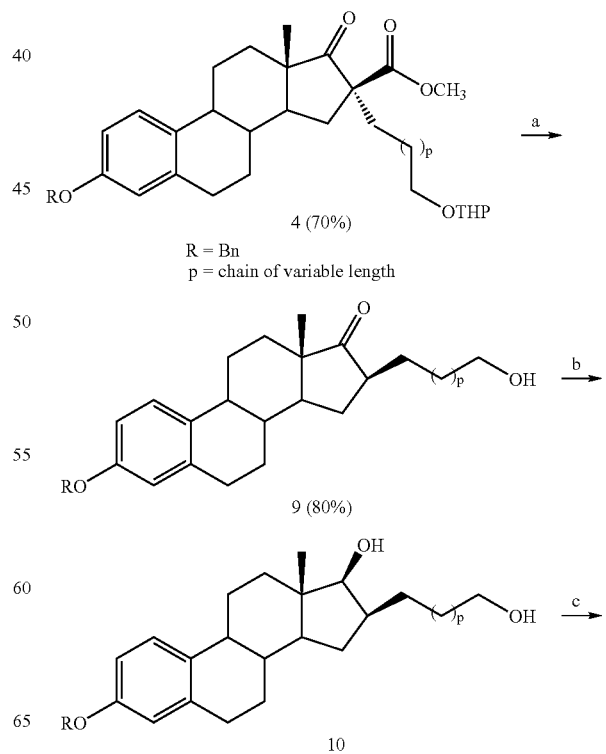

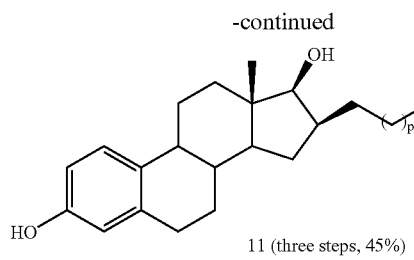

11 (three steps, 45%)

(yields are for p = 9)
o = 1 (example no. 7) or
o = 2 (example no. 6)

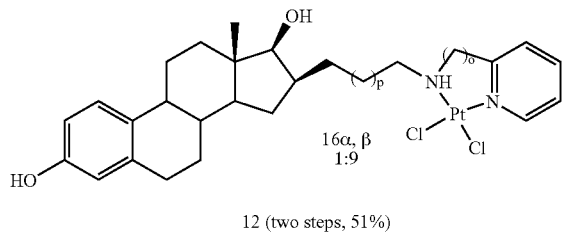

16α, β
1:9

12 (two steps, 51%)

Reagents:
(a) LiCl, DMF/H₂O, Δ, 20 h (known method of deprotection of THP);
(b) LiAlH₄, THF, -78° C. 1 h;
(c) 1) CBr₄, PPh₃, CH₂Cl₂, 22° C., 1 h; 2) H₂, 10% Pd/C, CH₃OH;
(d) 1) 2-(2'-aminoethyl) pyridine (p = 2) or 2-(aminomethyl) pyridine (p = 1), CH₃OH, Δ, 3 days; 2) K₂PtCl₄, DMF:H₂O, 25° C. 2-3 days.

Scheme 4 illustrates the reduction of derivative 5 (R=Bn) with lithium borohydride to give diol 13 (R=Bn) which could further be transformed into platinum (II) complexes possessing an hydroxy methyl function at position 16β according to the methodology described in this invention. Similarly, reduction of 5 (when R=THP) with lithium borohydride followed by deprotection of the tetrahydropyranyl group leads to the triol 13 (R=H) which is easily transmormed into the platinum (II) complexe of formula 14. This synthetic path leads to platinum (II) complexes linked at position 16α of the steroid nucleus (see compound 14).

Scheme 4 Reduction of β-cetoester 5 with LiBH₄ to give diol 13.

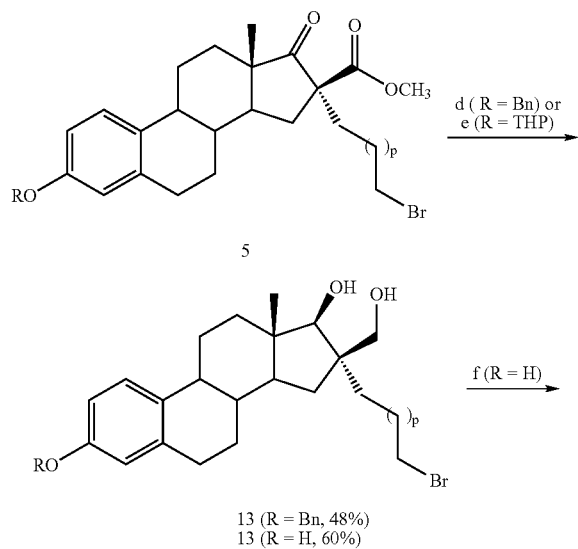

13 (R = Bn, 48%)
13 (R = H, 60%)

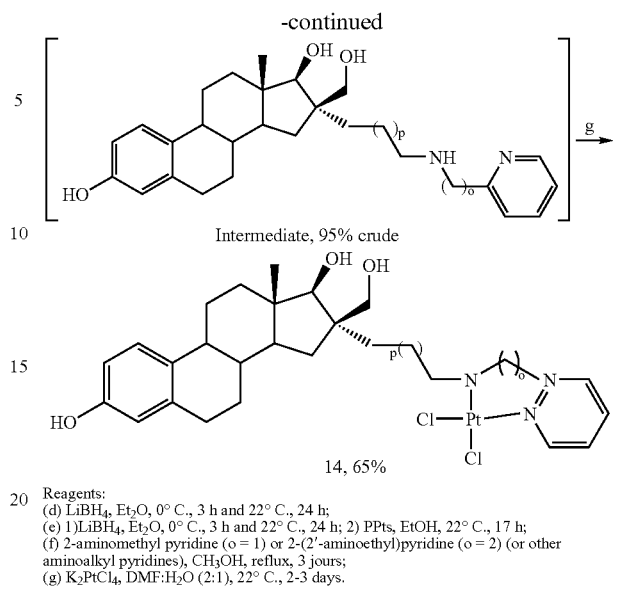

Intermediate, 95% crude 14, 65%

Reagents:
(d) LiBH₄, Et₂O, 0° C., 3 h and 22° C., 24 h;
(e) 1)LiBH₄, Et₂O, 0° C., 3 h and 22° C., 24 h; 2) PPts, EtOH, 22° C., 17 h;
(f) 2-aminomethyl pyridine (o = 1) or 2-(2'-aminoethyl)pyridine (o = 2) (or other aminoalkyl pyridines), CH₃OH, reflux, 3 jours;
(g) K₂PtCl₄, DMF:H₂O (2:1), 22° C., 2-3 days.

One of the problems associated with the Pt (II) derivatives is their low solubility. Therefore, in order to obtain estradiol-linked Pt (II) complexes with good solubility a PEG side chain can be used as the linking chain. The PEGs are ideal linkers because they are inexpensive, water soluble, and available in a variety of lengths. As shown on scheme 5, the di, tri-, tetra-, penta- and hexa-ethylene glycols were selected and will lead to linking arms containing 5, 8, 11, 14 and 17 atoms long. The ethylene glycols are monoprotected as tetrahydropyranyl ethers and the remaining alcohol are transformed into a good leaving group (either as a tosylate or as an iodide). The feasibility of this method was tested with tri-ethylene glycol, the iodo-tetrahydropyranyl ether was obtained with 40% overall yield (see scheme 5, series A). Alternatively, the PEGs could easily be transformed in a two-step reaction sequence into dibromides with an overall yield of 75% (see schema 5, series B). The PEG chains can be linked at position 16 of the steroid nucleus to give derivative of formula 6 (see scheme 2).

Scheme 5: Preparation of PEG side chains; iodo-THP (Series A), dibromide (Series B)

Series A:

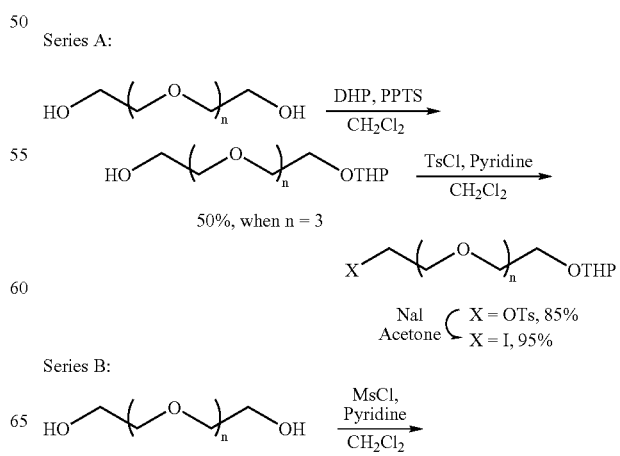

Series B:

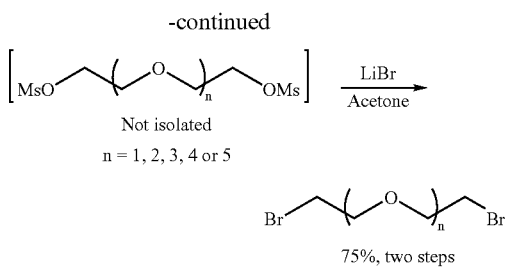

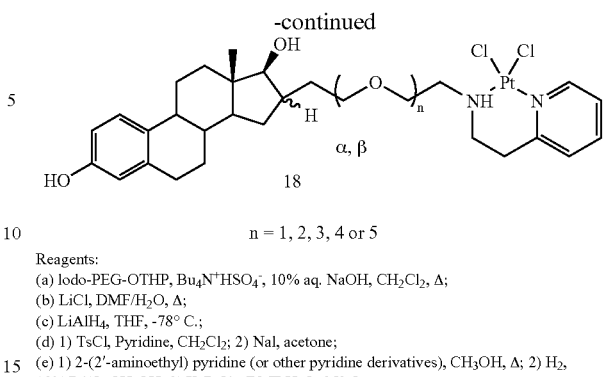

n = 1, 2, 3, 4 or 5

Reagents:
(a) Iodo-PEG-OTHP, Bu$_4$N$^+$HSO$_4^-$, 10% aq. NaOH, CH$_2$Cl$_2$, Δ;
(b) LiCl, DMF/H$_2$O, Δ;
(c) LiAlH$_4$, THF, -78° C.;
(d) 1) TsCl, Pyridine, CH$_2$Cl$_2$; 2) NaI, acetone;
(e) 1) 2-(2'-aminoethyl) pyridine (or other pyridine derivatives), CH$_3$OH, Δ; 2) H$_2$, 10% Pd/C, CH$_3$OH; 3) K$_2$PtCl$_4$, DMF:H$_2$O, 25° C.

Scheme 6 illustrates the initial steps towards the preparation of E$_2$-Pt (II) complexes linked with a PEG side chain at position 16α, β of the steroid nucleus. Several alternatives to this strategy can be envisioned by those skilled in the art. However, using a similar strategy as for the preparation of derivatives 12 (scheme 3), it is possible to link a PEG chain as it is shown on scheme 6.

Scheme 6: Synthesis of E$_2$-Pt (II) complexes with a PEG side chain

Compound 6 (R=THP and Y'=Br) is easily obtained from derivative 3 (R=THP) by alkylation with an appropriate α,ω-dibromo-PEG derivative (prepared as shown in scheme 5). Subsequent transformation of compound 6 (R=THP and Y'=Br) as described for the transformation of derivative 13 (R=H) into platinum (II) complexes 14 (see scheme 4) can produced a new series of platinum (II) complexes bearing a 16β-CH$_2$OH and a 16α-PEG side chain (for example compound 23, see example 15 of this invention).

Scheme 7 illustrates an alternate strategy for the preparation of E$_2$-Pt (II) complexes such as derivatives 12 starting from compound 8 (scheme 2). This strategy allows the formation of amide 21 which can be further transformed into platinum complexes 12. Other synthetic path for the synthesis of platinum (II) complexes, in accordance with this invention, can be envisioned by those skilled in the art.

Scheme 7: Synthesis of E$_2$-Pt (II) complexes via the diester 8

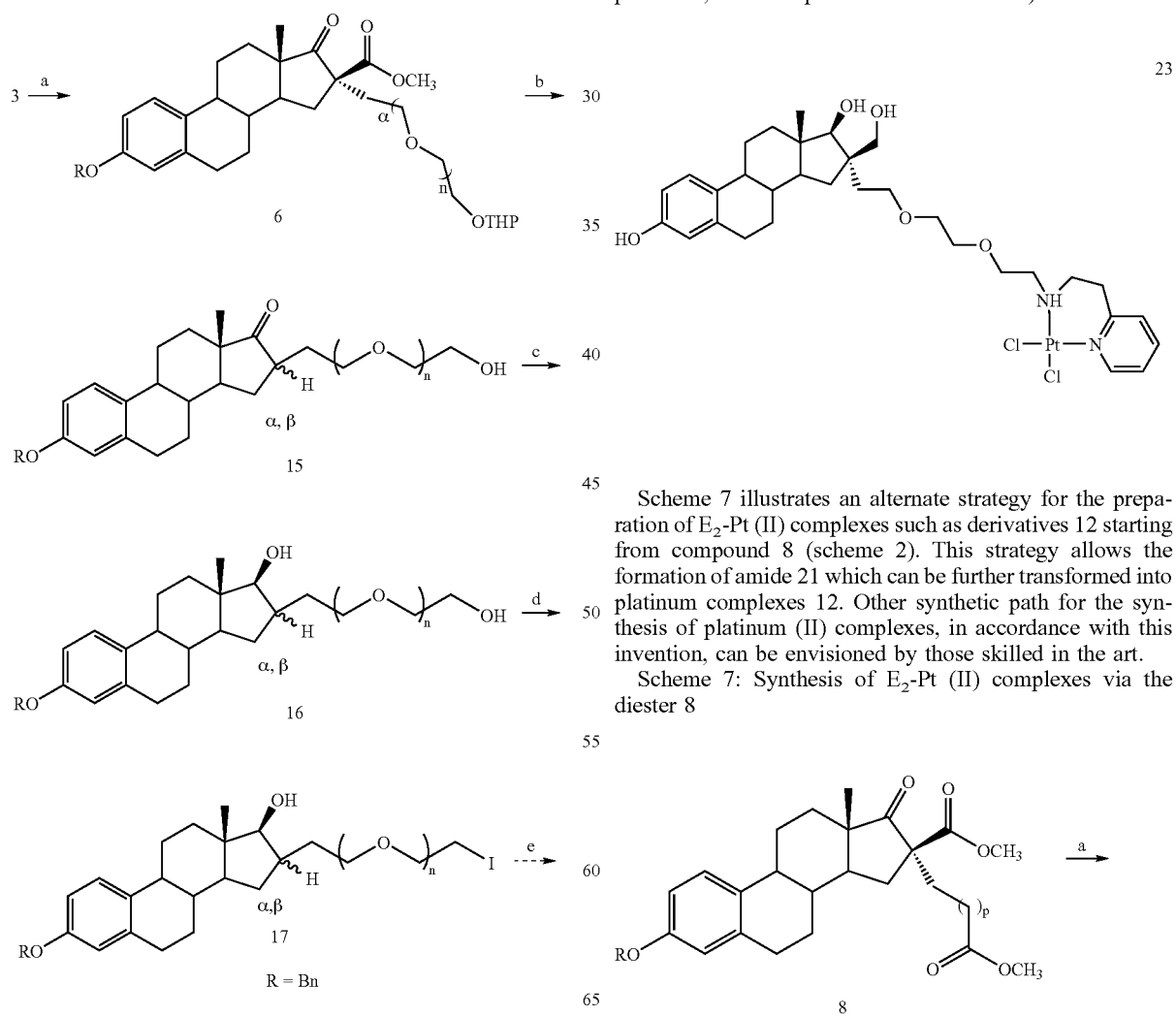

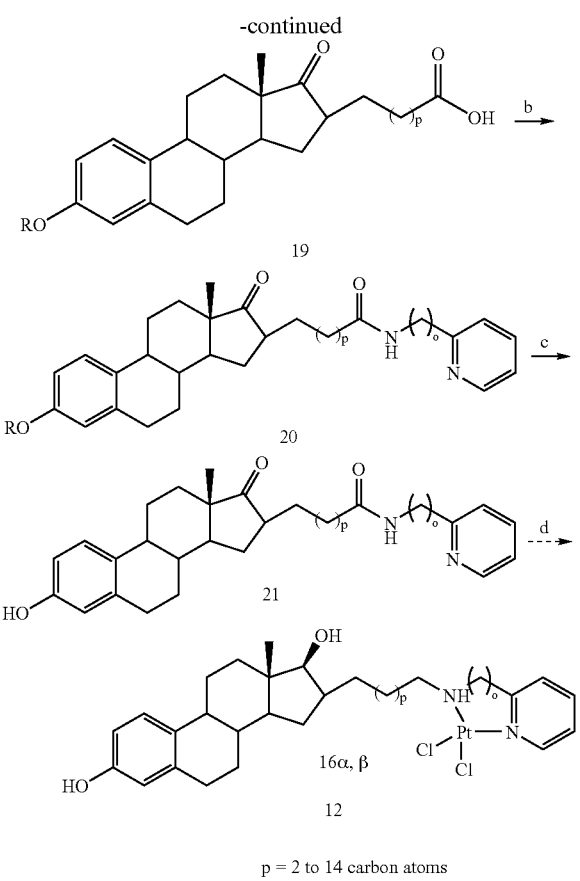

p = 2 to 14 carbon atoms

Reagents:
(a) LiCl, DMF/H$_2$O, Δ, 20 h;
(b) 1) ClCOCOCl, 22° C., 15 min; 2) 2-(2′-aminoethyl) pyridine (p = 2) or 2-(aminomethyl) pyridine (p =1) (or other aminoalkyl pyridine), CH$_2$Cl$_2$, 22° C., 1 h;
(c) H$_2$, 10% Pd/C, CH$_3$OH;
(d) 1) LiAlH$_4$, THF, -78° C., 20 h; 2) K$_2$PtCl$_4$, DMF:H$_2$O, 25° C., 2-3 days.

It is noteworthy, that the strategy developed at position 16 of the steroid nucleus could be used to functionnalized the known 6-keto-estradiol 22 to give new platinum (II) complexes linked at position 7α,β and 7α, with either a carbon atom or a PEG side chain. The 6-keto-estradiol derivative 22 can be purchase from Steraloid Inc. (catalog # E1350) or made from estradiol according to a known procedure (Tedesco, R., R. Fiaschi and E. Napolitano. *Synthesis*, 12, 1493–1495 (1995)).

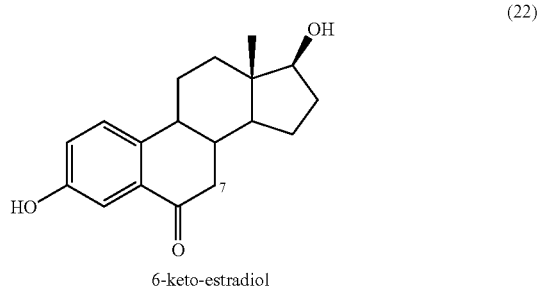

6-keto-estradiol

Moreover, methyl acrylate as well as various bromo (or iodo) esters can easily be linked using phase transfer catalytic reaction conditions on the estrone nucleus as it is presented on scheme 2. The resulting diester 7 and 8 can be further transformed into a variety of Pt (II) complexes using standard reaction conditions (see scheme 7, for the transformation of derivative 8).

As it can be appreciated by the skilled artisan, the above synthetic schemes are not intended to be a comprehensive list of all means by which the compounds described and claimed in this application may be synthesized. Further methods will be evident to those of ordinary skill in the art.

The compounds of this invention may be modified by appending appropriate functionalities to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

The compounds of this invention contain one or more asymmetric carbon atoms and thus may occur as racemates and racemic mixtures, single enantiomer, diastereomeric mixtures and individual diastereoisomers. All such isomeric forms of these compounds are expressly included in the present invention. Each stereogenic carbon may be of the R or S configuration.

In the description herein, the following abbreviations are used:

| Abbreviation | Meaning |
|---|---|
| Ac | Acetyl |
| AcOH | Acetic acid |
| cm | centimeter |
| DCM | Dichloromethane |
| DMF | Dimethylformamide |
| E$_1$ | Estrone |
| E$_2$ | Estradiol |
| ER+ | Estrogen receptor positive |
| ER− | Estrogen receptor negative |
| EtOAc | Ethyl acetate |
| EtOH | Ethyl alcohol |
| g | Gram |
| h | Hour |
| L | Liter |
| LAH | Lithium aluminum hydride |
| M | Molar |
| MeOH | Methyl alcohol |
| mg | Milligram |
| min | Minute |
| mol | Mole |
| mL | Milliliter |
| mmol | Millimole |
| MTT | 3-(4,5-Dimethylthiazol-2-yl)-2,5-diphenyltetrazolium bromide |
| N$_2$ | Nitrogen |
| PEG | Polyethylene glycol |
| PPTS | Pyridinium p-toluenesulfonate |
| SRB | Sulforhodamine B |
| THF | Tetrahydrofuran |
| THP | Tetrahydropyranyl |
| TLC | Thin layer chromatography |
| % v/v | Percent volume/volume |
| % w/v | Percent weight/volume |
| % w/w | Percent weight/weight |

EXAMPLES

This section describes the synthesis of several molecules that are presented in this document. These examples are for the purpose of illustration only and are not to be construed as limiting the scope of the invention in any way. This section presents the detailed synthesis of compounds type 12 (o=1 or 2), type 14 (with either an alkyl side chain or a PEG side chain). It also describes the synthesis of several key intermediates, which could be further transformed into new platinum (II) complexes.

Materials and Methods

Anhydrous reactions were performed under an inert atmosphere, the set-up assembled and cooled under dry nitrogen. Unless otherwise noted, starting material, reactant and solvents were obtained commercially and were used as such or purified and dried by standard means (D. D. Perrin and C. F. Armarego. Purification of Laboratory Chemicals (Third Edition), Pergamon Press, Oxford, N.Y. 1988). Organic solutions were dried over magnesium sulfate ($MgSO_4$), evaporated on a rotary evaporator and under reduced pressure. All reactions were monitored by UV fluorescence, or staining with iodine or spraying with an aqueous solution of phosphomolybdic acid followed by heating the plate around 135° C. Commercial TLC plates were Sigma T 6145 (polyester silica gel 60 Å, 0.25 mm). Preparative TLC was performed on 1 mm silica gel 60 Å, 20×20 plates (Whatman, 4861 840). Flash column chromatography was performed according to the method of Still and co-workers on Merck grade 60 silica gel, 230–400 mesh (W. C. Still, M. Kahn and A. Mitra. J. Org. Chem., 43, 2923 (1978)). All solvents used in chromatography had been distilled.

The infrared spectra were taken on a Nicolet Impact 420 FT-IR. Mass spectral assays were obtained using a VG Micromass 7070 HS instrument using ionization energy of 70 eV (University of Sherbrooke).

Nuclear magnetic resonance (NMR) spectra were recorded either on a Bruker AMX 500 equipped with a reversed or QNP probe (Pharmacor Inc) or (when indicated) on a Varian 200 MHz NMR apparatus. Samples were dissolved in deuterochloroform ($CDCl_3$), deuteroacetone (acetone-$d_6$) or deuterodimethylsulfoxide (DMSO-$d_6$) for data acquisition using tetramethylsilane or chloroform as internal standard (TMS, δ 0.0 ppm for $^1$H-NMR and $CDCl_3$ δ 77.0 ppm for $^{13}$C-NMR). Chemical shifts (δ) are expressed in parts per million (ppm), the coupling constants (J) are expressed in hertz (Hz). Multiplicities are described by the following abbreviations: s for singlet, d for doublet, dd for doublet of doublets, t for triplet, q for quartet, m for multiplet, #m· for several multiplets and br s for broad singlet.

General Procedures

General procedures for the preparation of the linking arms:

1. Conversion of bromoalcohols to bromo- or iodotetrahydropyranyl ethers (Y. He, S. Groleau, R. C.-Gaudreault, M. Caron, H.-M. Thérien, G. Bérubé, Bioorganic & Medicinal Chemistry Letters, 19, 2217–2222 (1995).

Step A. Synthesis of 1-tetrahydropyranyloxy-n-bromoalkane

A solution of commercially available bromoalcohol (27.6 mmol), dihydropyran (2.57 g, 30.6 mmol), and pyridinium p-toluenesulfonate (PPTS) (10 mg, 0.04 mmol) in dichloromethane (DCM, 50 mL) was stirred for 5 h under nitrogen. Afterwards, sodium bicarbonate ($NaHCO_3$, 500 mg) and $MgSO_4$ (5.0 g) were added to the reaction mixture and stirred 15 minutes before being filtered on a short pad of celite/silica gel (1 cm/4 cm) using DCM as the eluent. The filtrate was evaporated to a viscous oil (98% yield), which was used without further purification in the next step.

1-Tetrahydropyranyloxy-6-bromohexane (p=4)
IR (NaCl, $v_{max}$, $cm^{-1}$): 1170–1000 (C—O).
$^1$H-NMR ($CDCl_3$, δ ppm): 4.57 (1H, t, J=3.2 Hz, OCHO), 3.87, 3.74, 3.50 and 3.38 (4H, 4m, $CH_2OCHOCH_2$), 3.41 (2H, t, J=6.7 Hz, $CH_2Br$), 1.3–2.0 (14H, #m, 7×$CH_2$).

MS (m/e): 265 ($M^+$+1), 163 ($M^+$–OTHP).
1-Tetrahydropyranyloxy-8-bromooctane (p=6)
IR (NaCl, $v_{max}$, $cm^{-1}$): 1170–1000 (C—O).
$^1$H-NMR ($CDCl_3$, δ ppm): 4.58 (1H, t, J=3.5 Hz, OCHO), 3.87, 3.73, 3.50 and 3.38 (4H, 4m, $CH_2OCHOCH_2$), 3.41 (2H, t, J=6.8 Hz, $CH_2Br$), 1.2–2.0 (18H, #m, 9×$CH_2$—).
MS (m/e): 293 ($M^+$+1), 191 ($M^+$–OTHP).
1-Tetrahydropyranyloxy-10-bromodecane (p=8)
IR (NaCl, $v_{max}$, $cm^{-1}$): 1170–1000 (C—O).
$^1$H-NMR ($CDCl_3$, δ ppm): 4.58 (1H, t, J=3.5 Hz, OCHO), 3.87, 3.73, 3.50 and 3.38 (4H, 4m, $CH_2OCHOCH_2$), 3.41 (2H, t, J=6.8 Hz, $CH_2Br$), 1.2–2.0 (22H, #m, 11×$CH_2$).
MS (m/e): 321 ($M^+$+1), 219 ($M^+$–OTHP).
1-Tetrahydropyranyloxy-11-bromoundecane (p=9)
IR (NaCl, $v_{max}$, $cm^{-1}$): 1170–1000 (C—O).
$^1$H-NMR ($CDCl_3$, δ ppm): 4.56 (1H, t, J=3,1 Hz, OCHO), 3.87–3.34 (4H, 4m, $CH_2OCHOCH_2$), 3.39 (2H, t, J=6.8 Hz, $CH_2Br$), 1.86–1.27 (24H, #m, 12×$CH_2$).
$^{13}$C-NMR ($CDCl_3$, δ ppm): 98.8 (OCHO), 67.6 ($CH_2OCH$ on THP ring), 62.3 ($CH_2OCH$ on aliphatic chain), 33.9 ($CH_2Br$), 32.8, 30.8, 29.7, 29.5, 29.41, 29.36, 28.7, 28.1, 26.2, 25.5, 19.7.
MS (m/e): 335 ($M^+$+H+) and 233 ($M^+$–$C_5H_9O_2$).

Step B. Synthesis of 1-tetrahydropyranyloxy-n-iodoalkane.

Sodium iodide (6.07 g, 40.5 mmol) was added to a solution of the crude bromide (27 mmol) in dried acetone. The reaction mixture was stirred at 25° C. for 5 hrs. Then, most of the solvent was evaporated and the residue was transferred to an extraction flask with diethyl ether (150 mL) and water (100 mL). The organic phase was washed with water (6×50 mL), dried, filtered and concentrated to a viscous liquid. The crude iodide (98% yield) was used as such at the alkylation step.

1-Tetrahydropyranyloxy-6-iodohexane (p=4)
IR (NaCl, $v_{max}$, $cm^{-1}$): 1170–1000 (C—O).
$^1$H-NMR ($CDCl_3$, δ ppm): 4.57 (1H, t, J=3.2 Hz, OCHO), 3.87, 3.74, 3.50 and 3.38 (4H, 4m, $CH_2OCHOCH_2$), 3.19 (2H, t, J=7.0 Hz, $CH_2I$), 1.3–2.0 (14H, #m, 7×$CH_2$).
MS (m/e): 311 ($M^+$–H), 211 ($M^+$–OTHP).
1-Tetrahydropyranyloxy-8-iodooctane (p=6)
IR (NaCl, $v_{max}$, $cm^{-1}$): 1170–1000 (C—O).
$^1$H-NMR ($CDCl_3$, δ ppm): 4.58 (1H, t, J=3.5 Hz, OCHO), 3.87, 3.73, 3.50 and 3.38 (4H, 4m, $CH_2OCHOCH_2$), 3.19 (2H, t, J=7.0 Hz, $CH_2I$), 1.2–2.0 (18H, #m, 9×$CH_2$).
MS (m/e): 339 ($M^+$–H), 239 ($M^+$–OTHP).
1-Tetrahydropyranyloxy-10-iododecane (p=8)
IR (NaCl, $v_{max}$, $cm^{-1}$): 1170–1000 (C—O).
$^1$H-NMR ($CDCl_3$, δ ppm): 4.58 (1H, t, J=3.5 Hz, OCHO), 3.87, 3.73, 3.50 and 3.38 (4H, 4m, $CH_2OCHOCH_2$), 3.19 (2H, t, J=7.0 Hz, $CH_2I$), 1.2–2.0 (22H, #m, 11×$CH_2$).
MS (m/e): 367 ($M^+$–H), 267 ($M^+$–OTHP).
1-Tetrahydropyranyloxy-11-iodoundecane (p=9)
IR (NaCl, $v_{max}$, $cm^{-1}$): 1170–1000 (C—O).
$^1$H-NMR ($CDCl_3$, δ ppm): 4.58 (1H, t, J=3.5 Hz, OCHO), 3.87, 3.73, 3.50 and 3.38 (4H, 4m, $CH_2OCHOCH_2$), 3.19 (2H, t, J=7.0 Hz, $CH_2I$), 1.2–2.0 (24H, #m, 12×$CH_2$).
MS (m/e): 381 ($M^+$–H), 281 ($M^+$–OTHP).

2. Conversion of PEG to α-iodo-1-tetrahydropyranyloxy-PEG derivative (scheme 5, Series A)

This conversion is exemplified with tetra(ethylene glycol) (any commercially available PEG could be transformed using the same procedure).

Step A. Synthesis of 1-tetrahydropyranyloxy-3,6,9-trioxaundecan-11-ol (n=3)

A solution of tetra(ethylene glycol) (10.0 g, 51.5 mmol), 3,4-dihydro-2H-pyrane (3.3 mL, 36,1 mmol) and pyridinium p-toluenesulfonate (PPTS, 200 mg), in 100 mL DCM, was stirred at room temperature, under $N_2$, for 24 h. Then, sodium bicarbonate (1 g) and magnesium sulfate (1 g) are added to the reaction mixture and stirred for 15 min. The organic phase was filtered, dried and concentrated to an oil. Flash chromatography with a mixture of hexanes:acetone (7:3) gave the desired material in 50% yield.

IR (NaCl, $v_{max}$, cm$^{-1}$): 3700–3100 (O—H), 1125 (C—O).

$^1$H-NMR (CDCl$_3$, δ ppm): 4.64 (1H, t, J=3.0 Hz, OCHO), 3.91–3.40 (10H, m, 5×CH$_2$O), 3.68 (8H, s, 2×OCH$_2$CH$_2$O), 2.92 (1H, t, J=6.1 Hz, CH$_2$OH), 1.90–1.20 (6H, 3×m, CH$_2$CH$_2$CH$_2$).

$^{13}$C-NMR (CDCl$_3$, δ ppm): 98.7 (OCHO), 72.4 (CH$_2$OH) 70.4, 70.33, 70.28, 70.1, 66.4, 61.9, 61.4, 30.6, 30.3, 25.2, 19.2.

MS (m/e), C$_{13}$H$_{26}$O$_6$: 277 (M$^+$–H) and 195 (M$^+$–C$_5$H$_8$O).

Step B. Synthesis of 1-tetrahydropyranyloxy-11-tosyloxy-3,6,9-trioxaundecane (n=3)

A solution of 1-tetrahydropyranyloxy-3,6,9-trioxaundecan-11-ol (Step A, 5.54 g, 19.9 mmol), tosyl chloride (4.93 g, 25.9 mmol) and triethylamine (3.6 mL, 25.9 mmol) in 60 mL DCM, was stirred at 0° C., under $N_2$ for a period of 15 min and then at room temperature (22° C.) for a period of 24 h. Afterwards, the DCM was evaporated and diethyl ether was added to give a precipitate. The reaction mixture was filtered with diethyl ether (70 mL), evaporated and purified by flash chromatography with initially a mixture of hexanes:acetone (9:1) followed by a mixture of hexanes:acetone (3:2). The title compound was obtained as an oil in 85% yield.

IR (NaCl, $v_{max}$, cm$^{-1}$): 1600 (C=C), 1360 (SO$_2$), 1125 (C—O).

$^1$H-NMR (CDCl$_3$, δ ppm): 7.80 and 7.35 (4H, 2×d, J=8.2 Hz, 4H aromatic), 4.62 (1H, m, OCHO), 4.16 (2H, m, CH$_2$OTs), 3.91–3.46 (16H, m, 8×CH$_2$O), 3.59 (3H, s, CH$_3$), 1.90–1.20 (6H, m, CH$_2$CH$_2$CH$_2$).

MS (m/e), C$_{20}$H$_{32}$SO$_8$: no M$^+$, 348 (M$^+$–C$_5$H$_8$O).

Step C. Synthesis of 11-iodo-1-tetrahydropyranyloxy-3,6,9-trioxaundecane (n=3)

A solution of 1-tetrahydropyranyloxy-11-tosyloxy-3,6,9-trioxyundecane (Step B, 3.90 g, 9.0 mmol) and sodium iodide (2.70 g, 18.0 mmol) in dry acetone (40 mL), was stirred for 24 h under $N_2$, at room temperature (22° C.). Then, the acetone was evaporated. The residue was transferred into an extraction funnel with diethyl ether (60 mL) was washed subsequently with a sodium thiosulfate solution (5% w/v, 15 mL) and with water (5×70 mL). The ethereal phase was dried, filtered and concentrated to an oil (95% yield). This material was used as such at the alkylation step (see example 3).

IR (NaCl, $v_{max}$, cm$^{-1}$): 1125 (C—O).

$^1$H-NMR (CDCl$_3$, δ ppm): 4.63 (1H, t, J=3.6 Hz, OCHO), 3.87, 3.61 and 3.50 (4H, 3×m, CH$_2$OCHCH$_2$), 3.76 (2H, t, J=6.9 Hz, ICH$_2$CH$_2$O), 3.67 (10H, 2s, and m, 5×CH$_2$O), 3.26 (2H, t, J=6.9 Hz, ICH$_2$CH$_2$O), 1.90–1.50 (6H, 4×m, CH$_2$CH$_2$CH$_2$).

MS (m/e), C$_{13}$H$_{25}$IO$_5$: 389 (M$^+$+H$^+$), 305 (M$^+$+H$^+$—C$_5$H$_8$O).

3. Conversion of PEG to α,ω-dibromo-PEG derivative (Scheme 5, Series B)

A solution of a commercially available PEG (6.66 mmol) and triethylamine (2.32 ml, 16.65 mmol) in dry diethyl ether (10 ml) was cooled at 0° C., under a dry nitrogen atmosphere and treated dropwise with methanesulfonyl chloride (1.03 ml, 13.32 mmol). Stirring was continued for 1 h at 0° C. and at room temperature (22° C.) for 2 h. Afterwards, the diethyl ether was evaporated and dry acetone (12 ml) was added to the residue in order to precipitate most of the triethylamine hydrochloride salt, which was filtered from the solution. The filtrate, containing the dimesylate-PEG derivative was immediately treated with lithium bromide (2.31 g, 26.64 mmol) and heated to reflux for 20 h. Then the product was filtered on a small quantity of silica (3 cm) covered with celite (0.5 cm) with hexanes as the eluent. The filtrate was dried, filtered and evaporated to an oil. The α,ω-dibromo-PEG derivatives were obtained in 50 to 83% yield.

NB Some of these α,ω-dibromo-PEG derivatives are also commercially available.

1,5-dibromo-3-oxapentane (n=1)

50% yield

IR (NaCl, $v_{max}$, cm$^{-1}$): 1279 and 1117 (C—O).

$^1$H-NMR (CDCl$_3$, δ ppm): 3.83 (4H, t, J=6.3 Hz, 2×CH$_2$O), 3.47 (4H, t, J=6.3 Hz, 2×CH$_2$Br).

$^{13}$C-NMR (CDCl$_3$, δ ppm): 71.0 (CH$_2$O), 30.0 (CH$_2$Br).

1,8-dibromo-3,6-dioxaoctane (n=2)

69% yield

IR (NaCl, $v_{max}$, cm$^{-1}$): 1277 and 1121 (C—O).

$^1$H-NMR (CDCl$_3$, δ ppm): 3.80 (4H, t, J=6.2 Hz, BrCH$_2$CH$_2$O), 3.67 (4H, s, 2×CH$_2$O), 3.46 (4H, t, J=6.4 Hz, 2×CH$_2$Br).

$^{13}$C-NMR (CDCl$_3$, δ ppm): 71.2 (BrCH$_2$CH$_2$O), 70.4 (CH$_2$O), 30.3 (CH$_2$Br).

1,11-dibromo-3,6,9-trioxadecane (n=3)

71% yield

IR (NaCl, $v_{max}$, cm$^{-1}$): 1277 and 1116 (C—O).

$^1$H-NMR (CDCl$_3$, δ ppm): 3.80 (4H, t, J=6.3 Hz, 2×BrCH$_2$CH$_2$O), 3.66 (8H, s, 4×CH$_2$O), 3.46 (4H, t, J=6.3 Hz, 2×CH$_2$Br).

$^{13}$C-NMR (CDCl$_3$, δ ppm): 71.2 (BrCH$_2$CH$_2$O), 70.6 and 70.5 (CH$_2$O), 30.3 (CH$_2$Br).

1,14-dibromo-3,6,9,12-tetraoxatetradecane (n=4)

55% yield

IR (NaCl, $v_{max}$, cm$^{-1}$): 1277 and 1115 (C—O).

$^1$H-NMR (CDCl$_3$, δ ppm): 3.79 (4H, t, J=6.4 Hz, 2×BrCH$_2$CH$_2$O), 3.65 (12H, s, 6×CH$_2$O), 3.45 (4H, t, J=6.3 Hz, 2×CH$_2$Br).

$^{13}$C-NMR (CDCl$_3$, δ ppm): 71.1 (BrCH$_2$CH$_2$O), 70.6 and 70.53 and 70.48 (CH$_2$O), 30.3 (CH$_2$Br).

1,17-dibromo-3,6,9,12,15-pentaoxaheptadecane (n=5)

83% yield

IR (NaCl, $v_{max}$, cm$^{-1}$): 1277 and 1113 (C—O).

$^1$H-NMR (CDCl$_3$, δ ppm): 3.78 (4H, t, J=6.4 Hz, 2×BrCH$_2$CH$_2$O), 3.64 (16H, m, 8×CH$_2$O), 3.45 (4H, t, J=6.3 Hz, 2×CH$_2$Br).

$^{13}$C-NMR (CDCl$_3$, δ ppm): 71.1 (BrCH$_2$CH$_2$O), 70.6 and 70.52 and 70.47 (CH$_2$O), 30.2 (CH$_2$Br).

DETAILED DESCRIPTION OF THE INVENTION

EXAMPLES

The following compounds were prepared from estrone using the procedures summarized in schemes 2, 3, 4, 6 or 7.

Example 1

Preparation of 3-benzyloxy-16β-(methoxycarbonyl)-16α-(11'-tetrahydropyranyloxyundecanyl)-1,3,5(10)-estratrien-17-one (4)

Step A. Synthesis of 3-benzyloxy-1,3,5(10)-estratrien-17-one (2)

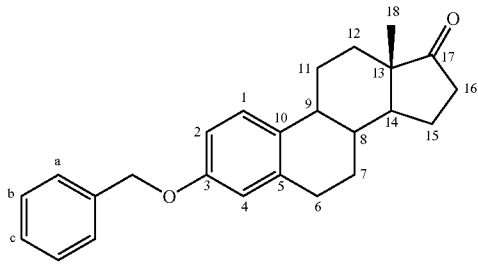

To a solution of estrone 1 (1.00 g, 3.70 mmol) in dichloromethane (10 mL), was added benzylbromide (0.53 mL, 4.44 mmol), tetrabutylammonium hydrogen sulfate (100 mg), and a solution of sodium hydroxide (10% w/v, 5 mL). The reaction mixture was stirred vigorously at reflux for 24 h. Then, the mixture was diluted with diethyl ether (30 mL) and water (30 mL) and washed with water (4×75 mL)'. The organic phase was dried with magnesium sulfate, filtered and evaporated to yield a solid compound. The residue was triturated with hexanes to give a white solid in 99% yield.

IR (KBr, $v_{max}$, cm$^{-1}$): 1731 (C=O), 1614 (C=C), 1230 and 1008 (C—O).

$^1$H-NMR (CDCl$_3$, δ ppm) 7.41 (2H, d, J=7.6 Hz, a-CH), 7.36 (2H, t, J=7.5 Hz, b-CH), 7.29 (1H, t, J=7.2 Hz, c-CH), 7.18 (1H, d, J=8.6 Hz, 1-CH), 6.78 (1H, dd, J=2.5 Hz and J=8.5 Hz, 2-CH), 6.71 (1H, d, J=2.1 Hz, 4-CH), 5.01 (2H, s, CH$_2$Ph), 2.88 (2H, m, 6-CH$_2$), 2.50–1.39 (13H, # m, 3×CH and 5×CH$_2$), 0.89 (3H, s, 18-CH$_3$).

$^{13}$C-NMR (CDCl$_3$, δ ppm): 220.5 (17-C), 156.8 (3-C), 137.7 (CCH$_2$O), 137.2 (5-C), 132.2 (10-C), 128.4 (b-C), 127.7 (c-C), 127.3 (a-C), 126.2 (1-C), 114.8 (4-C), 112.3 (2-C), 69.8 (CH$_2$Ph), 50.3 47.9, 43.9, 38.3, 35.8, 31.5, 29.6, 26.5, 25.8, 21.5, 13.8 (C-18).

MS (m/e): 360 (M$^+$), 269 (M$^+$–C$_7$H$_7$).

Exact mass calculated for C$_{25}$H$_{28}$O$_2$=360.2089; found=360.2095.

Step B. Synthesis of 3-benzyloxy-16α,β-(methoxycarbonyl)-1,3,5(10)-estratrien-17-one (3)

A solution of 3-benzyloxy-1,3,5(10)-estratrien-17-one (2) (4.00 g, 11.1 mmol) in dry THF (5 mL) was added over a period of 30 min to a solution of dimethylcarbonate (2.34 mL, 27.8 mmol) and potassium hydride (1.42 g, 34.7 mmol) in dry THF (40 mL). Then, the mixture was heated to reflux for a period of 3 h. Most of the solvent was then evaporated and the residue was diluted with ethyl acetate (100 mL) and treated with a saturated ammonium chloride solution (50 mL). The organic phase was washed with water (6×40 mL), dried and evaporated to give a yellowish solid. Trituration of the residue with a mixture of acetone:hexanes (1:1) yielded the title compound in 90% yield as a white solid.

IR (NaCl, $v_{max}$, cm$^{-1}$): 1747 (C=O, ester), 1721 (C=O, ketone), 1609 (C=C), 1226 (C—O).

$^1$H-NMR (CDCl$_3$, δ ppm): 7.46 (2H, d, J=7.4 Hz, a-CH), 7.41 (2H, t, J=7.5 Hz, b-CH), 7.35 (1H, t, J=7.2 Hz, c-CH), 7.22 (1H, d, J=8.7 Hz, 1-CH), 6.83 (1H, dd, J=2.5 Hz and J=8.5 Hz, 2-CH), 6.77 (1H, s, 4-CH), 5.06 (2H, s, CH$_2$Ph), 3.79 (3H, s, COOCH$_3$), 3.24 (1H, t, J=9.2 Hz, 16β-CH), 2.92 (2H, m, 6-CH$_2$), 1.31–2.46 (11H, #m, 3×CH, 4×CH$_2$), 1.02 and 0.99 (3H, 2s, 18-CH$_3$, 16α,β (4:1)).

$^{13}$C-NMR (CDCl$_3$, δ ppm), major isomer 16α-CO$_2$CH$_3$: 211.9 (17-C), 169.8 (COOCH$_3$), 156.9 (3-C), 137.6 (CCH$_2$O), 137.1 (5-C), 131.9 (10-C), 128.4 (b-C), 127.8 (c-C), 127.3 (a-C), 126.2 (1-C), 114.8 (4-C), 112.4 (2-C), 69.8 (CH$_2$Ph), 54.0 (COOCH$_3$), 52.4, 48.8, 47.8, 43.9, 37.8, 31.8, 29.5, 26.4, 26.3, 25.7, 13.2 (18-C).

MS (m/e): 418 (M$^+$), 386 (M$^+$–CH$_3$O).

Exact mass: calculated for C$_{27}$H$_{30}$O$_4$=418.2144; found=418.2136.

Step C. Synthesis of 3-benzyloxy-16β-(methoxycarbonyl)-16α-(11'-tetrahydropy-ranyloxyundecanyl)-1,3,5(10)-estratrien-17-one (4)

A stirred solution of derivative 3 (0.98 g, 2.33 mmol), 1-tetrahydropyranyloxy-11-bromoundecane (3.12 g, 9.32 mmol), benzyltriethylammonium chloride (150 mg) and sodium hydroxide 10% w/v (8 mL) in dichloromethane (12 mL) was heated to reflux for 20 h. Then, the mixture was diluted with diethyl ether (40 mL) and extracted with a saturated ammonium chloride solution (2×20 mL) and with water (4×50 mL). The organic phase was dried, filtered and concentrated to an oil. Purification by flash chromatography with a mixture of hexanes and acetone (9:1) gave 1.12 g (70%) of viscous oil.

IR (NaCl, $v_{max}$, cm$^{-1}$): 1747 (C=O, ester), 1722 (C=O, ketone), 1604 (C=C), 1231 and 1031 (C—O).

$^1$H-NMR (CDCl$_3$, δ ppm): 7.43 (2H, d, J=7.6 Hz, a-CH), 7.38 (2H, t, J=7.4 Hz, b-CH), 7.32 (1H, t, J=7.3 Hz, c-CH), 7.19 (1H, d, J=8.5 Hz, 1-CH), 6.79 (1H, dd, J=2.0 Hz and J=8.8 Hz, 2-CH), 6.74 (1H, s, 4-CH), 5.04 (2H, s, CH$_2$Ph), 4.58 (1H, t, J=3.6 Hz, OCHO), 3.90–3.36 (4H, 4m, CH$_2$OCHOCH$_2$) 3.73 (3H, s, COOCH$_3$), 2.91 (2H, m, 6-CH$_2$), 2.41–1.20 (37H, #m, 3×CH, 17×CH$_2$), 0.93 and 0.91 (3H, 2s, 18-CH$_3$, 16α,β (6:1)).

$^{13}$C-NMR (CDCl$_3$, δ ppm), major isomer 16β-CO$_2$CH$_3$: 214.0 (17-C), 171.8 (COOCH$_3$), 156.9 (3-C), 137.7 (CCH$_2$O), 137.2 (5-C), 132.1 (10-C), 128.5 (b-C), 127.8 (c-C), 127.4 (a-C), 126.2 (1-C), 114.8 (4-C), 112.4 (2-C), 98.8 (OCHO), 69.9 (CH$_2$Ph), 67.6 (CH$_2$OCH on THP ring), 62.3 (CH$_2$OCH on aliphatic chain), 60.1, 52.5 (COOCH$_3$), 50.4, 49.4, 45.9, 44.0, 37.9, 35.5, 32.0, 31.5, 30.7, 30.5, 29.74, 29.70, 29.5, 29.4, 29.3, 26.5, 26.2, 25.7, 25.5, 25.4, 19.7, 14.0 (18-C).

MS (m/e): 672 (M$^+$), 587 (M$^+$–C$_5$H$_9$O), 497 (M$^+$–C$_5$H$_8$O and C$_7$H$_7$).

Exact mass: calculated for C$_{43}$H$_{60}$O$_6$=672.4390; found=672.4398.

Example 2

Preparation of 3-benzyloxy-16β-(methoxycarbonyl)-16α-(111'-bromoundecanyl)-1,3,5(10)-estratrien-17-one (5)

A mixture of β-cetoester 3 (0.15 g, 0.36 mmol), 1,11-dibromoundecane (0.42 mL, 1.80 mmol), benzyltriethylammonium chloride (50 mg), sodium hydroxide 10% w/v (3 mL), and dichloromethane (5 mL), was heated to reflux for 20 h. Afterwards, the reaction mixture was diluted with diethyl ether (40 mL) and washed with a saturated ammonium chloride solution (2×20 mL) and with water (4×50 mL). The organic phase was dried, filtered and concentrated to an oil. Flash chromatography with a mixture of hexanes:acetone (9:1) gave 76% of the desired material (5) as an oil. The 16α-bromoundecanyl side chain was obtained stereospecifically.

IR (NaCl, $\nu_{max}$, cm$^{-1}$): 1747 (C=O, ester), 1722 (C=O, ketone), 1604 (C=C), 1012 (C—O).

$^1$H-NMR (CDCl$_3$, δ ppm): 7.44 (2H, d, J=7.5 Hz, a-CH), 7.39 (2H, t, J=7.4 Hz, b-CH), 7.33 (1H, t, J=7.1 Hz, c-CH), 7.21 (1H, d, J=8.5 Hz, 1-CH), 6.80 (1H, d, J=8.7 Hz, 2-CH), 6.76 (1H, s, 4-CH), 5.05 (2H, s, CH$_2$Ph), 3.74 (3H, s, COOCH$_3$), 3.42 (2H, t, J=6.8 Hz, CH$_2$Br), 2.94–2.91 (2H, m, 6-CH$_2$), 2.43–1.22 (31H, #m, 3×CH, 14×CH$_2$), 0.95 (3H, s, 18-CH$_3$).

$^{13}$C-NMR (CDCl$_3$, δ ppm): 214.0 (17-C), 171.9 (COOCH$_3$), 156.9 (3-C), 137.7 (CCH$_2$O), 137.2 (5-C), 132.1 (10-C), 128.5 (b-C), 127.8 (c-C), 127.4 (a-C), 126.2 (1-C), 114.9 (4-C), 112.4 (2-C), 69.9 (CH$_2$Ph), 60.1, 52.5 (COOCH$_3$), 49.5, 45.9, 44.0, 37.9, 35.5, 34.0, 32.8, 32.1, 30.5, 29.7, 29.5, 29.4, 29.35, 29.3, 28.7, 28.1, 26.5, 25.7, 25.4, 14.0 (18-C).

MS (m/e): 650 (M$^+$), 500 (M$^+$–C$_2$H$_3$O$_2$ and C$_7$H$_7$).

Exact mass: calculated for C$_{38}$H$_{51}$O$_4$=650.2970; found=650.2982.

Example 3

Preparation of 3-benzyloxy-16β-(methoxycarbonyl)-16α-(11'-tetrahydropyranyloxy-3',6',9'-trioxaundecanyl)-1,3,5(10)-estratrien-17-one (6)

A solution of β-cetoester 3 (0.28 g, 0.67 mmol), 11-iodo-1-tetrahydropyranyloxy-3,6,9-trioxaundecane (0.65 g, 1.67 mmol), benzyltriethylammonium chloride (100 mg) and sodium hydroxide 10% w/v (4 mL), in 6 mL DCM, was stirred vigorously and heated to reflux for 20 h. The reaction mixture was diluted with diethyl ether (40 mL) and extracted with a hydrochloric acid solution 10% v/v (2×20 mL) and with water (4×50 mL). The organic phase was filtered, dried and evaporated to an oil. The crude material was purified by flash chromatography with a mixture of hexanes acetone (8.5:1.5) to give a separable mixture of 16α (51%) and 16β (13%) PEG side chain (overall yield=64%).

IR (NaCl, $\nu_{max}$, cm$^{-1}$): 1742 (C=O, ester), 1717 (C=O, ketone), 1600 (C=C), 1031 (C—O).

$^1$H-NMR (CDCl$_3$, δ ppm): 7.42 (2H, d, J=7.5 Hz, a-CH), 7.38 (2H, t, J=7.6 Hz, b-CH), 7.31 (1H, t, J=7.2 Hz, c-CH), 7.18 (1H, d, J=8.7 Hz, 1-CH), 6.79 (1H, dd, J=2.6 Hz and J=8.7 Hz, 2-CH), 6.73 (1H, d, J=2.0 Hz, 4-CH), 5.03 (2H, s, CH$_2$Ph), 4.63 (1H, t, J=3.6 Hz, OCHO), 3.89–3.45 (16H, #m, 8×CH$_2$O) 3.72 (3H, s, COOCH$_3$), 2.91–2.88 (2H, m, 6-CH$_2$), 2.40–1.41 (19H, #m, CH$_2$CH$_2$CH$_2$, 16-CCH$_2$CH$_2$O, 3×CH, 4×CH$_2$), 0.95 (3H, s, 18-CH$_3$, 16α PEG side chain).

$^{13}$C-NMR (CDCl$_3$, δ ppm): 213.9 (17-C), 171.8 (COOCH$_3$), 156.9 (3-C), 137.7 (CCH$_2$O), 137.2 (5-C), 132.1 (10-C), 128.5 (b-C), 127.8 (c-C), 127.4 (a-C), 126.2 (1-C), 114.9 (4-C), 112.4 (2-C), 98.9 (OCHO), 70.6, 70.5, 70.2, 69.9 (CH$_2$Ph), 67.8 (CH$_2$OCH of THP ring), 66.6, 62.2 (CH$_2$OCH side chain), 61.7, 58.2, 52.6 (COOCH$_3$), 49.4, 45.9, 44.0, 37.9, 34.8, 32.2, 31.0, 29.7, 29.5, 26.5, 25.7, 25.4, 19.6, 14.1 (18-C).

MS (m/e): 696 (M$^+$+NH$_4^+$), 595 (M$^+$+NH$_4^+$–C$_5$H$_9$O$_2$).

Exact mass calculated for C$_{40}$H$_{58}$NO$_9$ (M$^+$+NH$_4^+$) 696.4099; found=696.4111.

Example 4

Preparation of 3-benzyloxy-16β-methoxycarbonyl-16α-[2'-(methoxycarbonyl)ethyl]-1,3,5(10)-estratrien-17-one (7)

A solution of β-cetoester 3 (490 mg, 1.18 mmol), methyl acrylate (1.21 g, 14.18 mmol), tetrabutylammonium hydrogensulfate (100 mg, 0.29 mmol) and sodium hydroxide 10% w/v (6 ml), in 8 mL DCM, was stirred vigorously and heated to reflux for 18 h. The reaction mixture was diluted with ethyl acetate (25 mL) and extracted with a saturated ammonium chloride solution (2×20 mL) and with water (4×50 mL). The organic phase was filtered, dried and evaporated to an oil. The crude material was purified by flash chromatography with a mixture of hexanes:acetone (4:1) to give a 94% of the desired diester as a single isomer.

IR (NaCl, $\nu_{max}$, cm$^{-1}$): 1731 (C=O, esters and ketone), 1010 and 1210 (C—O).

$^1$H-NMR (CDCl$_3$, δ ppm): 7.43 (2H, d, J=7.4 Hz, a-CH), 7.39 (2H, t, J=7.4 Hz, b-CH), 7.33 (1H, d, J=7.1 Hz, c-CH), 7.20 (1H, d, J=8.9 Hz, 1-CH), 6.80 (1H, dd, J=2.1 and 8.7 Hz, 2-CH), 6.74 (1H, s, 4-CH), 5.04 (2H, s, CH$_2$Ph), 3.74 (3H, s, CCOOCH$_3$), 3.68 (3H, s, CH$_2$COOCH$_3$), 2.90 (2H, m, 6-CH$_2$), 2.50–1.30 (15H, #m, 6×CH$_2$, 3×CH), 0.98 (3H, s, 18-CH$_3$).

$^{13}$C-NMR (CDCl$_3$, δ ppm): 214.1 (C-17), 173.4 (CCOOCH$_3$), 171.7 (CH$_2$COOCH$_3$), 157.0 (C-3), 137.7 (CCH$_2$O), 137.3 (C-5), 132.1 (C-10), 128.7 (C-b), 127.9 (C-c), 127.5 (C-a), 126.4 (C-1), 114.9 (C-4), 112.5 (C-2), 70.0 (CH$_2$Ph), 59.0 (C-16), 52.9 (CCOOCH$_3$), 51.9 (CH$_2$COOCH$_3$), 49.8 (C-13), 46.3 (C-14), 44.1 (C-9), 37.9 (C-8), 32.2, 31.9, 30.2, 30.1, 29.7, 26.6, 25.8, 14.2 (C-18).

MS (m/e): 504 (M$^+$), 473 (M$^+$–CH$_3$O).

Exact mass: calculated for C$_{31}$H$_{36}$O$_6$=504.2512; found=504.2503.

Example 5

Preparation of 3-benzyloxy-16β-(methoxycarbonyl)-16α-(10'-methoxycarbonyldecanyl)-1,3,5(10)-estratrien-17-one (8, p=9)

Step A. Synthesis of methyl 11-iodoundecanoate

To a solution of commercially available methyl 11-bromoundecanoate (5.80 g, 20.8 mmol) dissolved in dry acetone (70 mL) was added sodium iodide (4.05 g, 27.0 mmol). The reaction mixture was stirred at room temperature (22° C.) for 19 h under an inert nitrogen atmosphere. Afterwards, the acetone was evaporated and the residue transferred into an extraction funnel with diethyl ether (100 mL) and water (40 mL). The organic phase was washed with a thiosulfate solution (5% w/v, 2×20 mL) and with water 3×40 mL. The organic phase was dried, filtered on a short column of celite and celica (1 cm/4 cm) with a mixture of hexanes:acetone as the eluent. Evaporation of the solvent gave the title compound (95%) as an oil, which was used without further purification at the next step.

IR (NaCl, $\nu_{max}$, cm$^{-1}$): 1731 (C=O), 1200 and 1164 (C—O).

$^1$H-NMR (200 MHz, CDCl$_3$, δ ppm): 3.67 (3H, s, CH$_3$), 3.19 (2H, t, J=7.0 Hz, CH$_2$I), 2.30 (2H, t, J=7.4 Hz, RCH$_2$COOCH$_3$), 1.85–1.75 (2H, m, ICH$_2$CH$_2$R), 1.66–1.58 (2H, m, RCH$_2$CH$_2$COOCH$_3$), 1.43–1.29 (12H, br s, 6×CH$_2$).

MS (m/e): 327 (M$^+$+H$^+$), 295 (M$^+$–OCH$_3$).

Exact mass: calculated for $C_{11}H_{24}IO_2$ (M$^+$+H$^+$) =327.0821; found=327.0813.

Step B. Synthesis of 3-benzyloxy-16β-(methoxycarbonyl)-16α-(10'-methoxycarbonyldecanyl)-1,3,5(10)-estratrien-17-one (8, p=9)

A solution of β-cetoester 3 (0.26 g, 0.62 mmol), methyl 11-iodoundecanoate (0.81 g, 2.48 mmol), benzyltriethylammonium chloride (100 mg) and sodium hydroxide 10% w/v (4 mL), in 6 mL DCM, was stirred vigorously and heated to reflux for 20 h. The reaction mixture was diluted with ethyl acetate (40 mL) and extracted with a saturated ammonium chloride solution (2×20 mL) and with water (4×20 mL). The organic phase was filtered, dried and evaporated to an oil. The crude material was purified by flash chromatography with a mixture of hexanes:acetone (9:1) to give a stereospecifically the 16α alkylated product (87%).

IR (NaCl, $v_{max}$, cm$^{-1}$): 1731 (C=O), 1604 and 1568 (C=C), 1011 (C—O).

$^1$H-NMR (CDCl$_3$, δ ppm): 7.43 (2H, d, J=7.4 Hz, a-CH), 7.38 (2H, t, J=7.4 Hz, b-CH), 7.32 (1H, t, J=7.1 Hz, c-CH), 7.19 (1H, d, J=8.6 Hz, 1-CH), 6.79 (1H, d, J=8.2 Hz, 2-CH), 6.74 (1H, s, 4-CH), 5.04 (2H, s, CH$_2$Ph), 3.73 (3H, s, 16β-CO$_2$CH$_3$), 3.67 (3H, s, 16α-(CH$_2$)$_{10}$CO$_2$CH$_3$), 2.91 (2H, m, 6-CH$_2$), 2.30 (2H, t, J=7.4 Hz, RCH$_2$COOCH$_3$), 2.42–1.21 (29H, #m, 3×CH and 13×CH$_2$), 0.93 (3H, s, 18-CH$_3$).

$^{13}$C-NMR (CDCl$_3$, δ ppm): 214.0 (17-C), 174.2 ((CH$_2$)$_{10}$COOCH$_3$), 171.8 (COOCH$_3$), 156.8 (3-C), 137.6 (CCH$_2$O), 137.2 (5-C), 132.1 (10-C), 128.5 (b-C), 127.8 (c-C), 127.3 (a-C), 126.2 (1-C), 114.8 (4-C), 112.4 (2-C), 69.9 (CH$_2$Ph), 60.1, 52.5 (CO$_2$CH$_3$), 51.3 ((CH$_2$)$_{10}$CO$_2$CH$_3$), 49.4, 45.9, 44.0, 37.9, 35.5, 34.0, 32.0, 30.5, 29.7, 29.5, 29.4, 29.3, 29.2, 29.1, 29.0, 26.5, 25.7, 25.4, 24.9, 14.0 (18-C).

MS (m/e): 616 (M$^+$), 585 (M$^+$−OCH$_3$), 525 (M$^+$−C$_7$H$_7$).
Exact mass: calculated for $C_{39}H_{52}O_6$=616.3764; found=616.3759.

Example 6

Preparation of 16β-[11'-(2''-pyridylethylamino)undecanyl]-1,3,5(10)-estratrien-3,17β-diol dichloroplatinate (11) (12, o=2, p=9)

Step A. Synthesis of 3-benzyloxy-16β-(11'-hydroxyundecanyl)-1,3,5(10)-estratrien-17-one (9, p=9)

A solution of 3-benzyloxy-16β-(methoxycarbonyl)-16α-(11'-tetrahydropyranyloxyundecanyl)-1,3,5(10)-estratrien-17-one (4, example 1) (0.41 g, 0.61 mmol), lithium chloride (0.57 g, 13.37 mmol), and water (0.24 mL, 13.37 mmol) in N,N-dimethylformamide (8 mL) was stirred and heated to reflux for 20 h. Afterwards, the solvent was partly evaporated and the residue transferred into an extraction funnel using ethyl acetate (40 mL) and water (30 mL). The organic phase was washed twice with hydrochloric acid (20 mL, 10% v/v) and with water 4×50 mL. The organic phase was dried, filtered and concentrated to an oil. Purification by flash chromatography with a mixture of hexanes and acetone (9:1) gave 80% of the final product.

IR (NaCl, $v_{max}$, cm$^{-1}$): 3200–3600 (O—H), 1731 (C=O), 1604 (C=C), 1231 and 1021 (C—O).

$^1$H-NMR (CDCl$_3$, δ ppm): 7.45 (2H, d, J=7.3 Hz, a-CH), 7.39 (2H, t, J=7.4 Hz, b-CH), 7.33 (1H, t, J=7.3 Hz, c-CH), 7.21 (1H, d, J=8.6 Hz, 1-CH), 6.80 (1H, dd, J=2.0 Hz and J=8.8 Hz, 2-CH), 6.75 (1H, s, 4-CH), 5.05 (2H, s, CH$_2$Ph), 3.65 (2H, t, J=6.6 Hz, CH$_2$OH), 2.91 (2H, m, 6-CH$_2$), 2.47–1.25 (33H, #m, 4×CH, 14×CH$_2$, OH), 0.96 and 0.88 (3H, 2s, 18-CH$_3$, 16α,β (1:1.7)).

MS (m/e): 530 (M$^+$+H$^+$), 439 (M$^+$−C$_7$H$_6$).
Exact mass calculated for $C_{36}H_{50}O_3$ (M$^+$+H$^+$)=530.3768; found=530.3760.

Step B. Synthesis of 3-benzyloxy-16β-(11'-hydroxyundecanyl)-1,3,5(10)-estratrien-17β-ol (10, p=9)

To a solution of derivative 9 (step A, 0.23 g, 0.43 mmol) in dry THF (8 mL) at −78° C. under an inert nitrogen atmosphere, was slowly added a solution of lithium aluminum hydride 1M/THF (4.3 mL, 4.3 mmol). The resulting mixture was stirred for 1 h. Then, ethyl acetate (1 mL) was added to destroy the excess LiAlH$_4$. The reaction mixture was diluted with ethyl acetate (40 mL), extracted with a solution of hydrochloric acid (10% v/v, 3×20 mL) and with water (5×50 mL). The organic phase was dried, filtered and evaporated to an oil. Purification by flash chromatography with a mixture of hexanes and acetone (4:1) gave a total of 0.18 g (78%) of viscous oil. The two isomers were isolated 60% (0.14 g) of the 16α isomer and 18% (0.04 g) of the 16β isomer.

IR (NaCl, $v_{max}$, cm$^{-1}$): 3650–3100 (O—H), 1609 (C=C), 1221 and 1022 (C—O).

$^1$H-NMR (CDCl$_3$, δ ppm): 7.44 (2H, d, J=7.5 Hz, a-CH), 7.38 (2H, t, J=7.4 Hz, b-CH), 7.32 (1H, t, J=7.2 Hz, c-CH), 7.19 (1H, d, J=8.6 Hz, 1-CH), 6.78 (1H, dd, J=1.9 Hz and 8.1 Hz, 2-CH), 6.72 (1H, d, J=0.8 Hz, 4-CH), 5.03 (2H, s, CH$_2$Ph), 3.79 (1H, d, J=11.2 Hz, CHOH), 3.62 (2H, t, J=6.7 Hz, CH$_2$OH), 3.50 (1H, d, J=10.9 Hz, CHOH, 16α), 3.45 (1H, s, CH$_2$OH), 2.82–2.80 (2H, m, 6-CH$_2$), 2.30–1.07 (32H, #m, 4×CH, 14×CH$_2$), 0.88 (3H, s, 18-CH$_3$, 16α).

$^{13}$C-NMR (CDCl$_3$, δ ppm), 16α pure isomer: 156.7 (3-C), 137.9 (CCH$_2$O), 137.2 (5-C), 132.9 (10-C), 128.5 (b-C), 127.8 (c-C), 127.4 (a-C), 126.2 (1-C), 114.8 (4-C), 112.2 (2-C), 90.5 (CHOH), 69.9 (CH$_2$Ph), 62.9 (CH$_2$OH), 47.6, 46.7, 44.8, 43.8, 39.3, 37.92, 37.89, 33.1, 32.7, 30.5, 29.7, 29.59, 29.57, 29.5, 29.3, 27.4, 26.2, 25.7, 24.7, 11.9 (18-C).

MS (m/e): 532 (M$^+$), 423 (M$^+$−H$_2$O and C$_7$H$_7$).
Exact mass: calculated for $C_{36}H_{52}O_3$=532.3905; found=532.3916.

Step C. Synthesis of 3-benzyloxy-16β-(11'-bromoundecanyl)-1,3,5(10)-estratrien-17β-ol (precursor of derivative 11, p=9)

The diol 10 (0.16 g, 0.30 mmol) was solubilized in dichloromethane (10 mL), then carbon tetrabromide (0.40 g, 1.20 mmol) and triphenylphosphine (0.31 g, 1.20 mmol) are added to the diol. The reaction mixture under an inert atmosphere of nitrogen was stirred at room temperature for 1 to 2 h. The organic phase was diluted with diethyl ether (50 mL) and washed with a saturated ammonium chloride solution (25 mL) and with water (5×60 mL). The ethereal phase was dried, filtered and evaporated to an oil. The residue was purified by flash chromatography with a mixture of hexanes and acetone (9:1) to give 0.11 g (64%) of the title.

IR (NaCl, $v_{max}$, cm$^{-1}$): 3650–3150 (O—H), 1604 (C=C), 1232 and 1022 (C—O).

$^1$H-NMR (CDCl$_3$, δ ppm): 7.47 (2H, d, J=7.4 Hz, a-CH), 7.42 (2H, t, J=7.5 Hz, b-CH), 7.35 (1H, t, J=7.1 Hz, c-CH), 7.24 (1H, d, J=8.5 Hz, 1-CH), 6.83 (1H, dd, J=1.7 Hz and 8.1 Hz, 2-CH), 6.76 (1H, s, 4-CH), 5.07 (2H, s, CH$_2$Ph), 3.77 (0.7H, d, J=10.1 Hz, CHOH, 16β), 3.44 (2H, t, J=6.9 Hz, CH$_2$Br), 3.30 (0.3H, d, J=7.6 Hz, CHOH, 16α), 2.89 (2H, m, 6-CH$_2$), 2.35–1.02 (33H, #m, 4×CH, 14×CH$_2$, —OH), 0.80 and 0.78 (3H, 2s, 18-CH$_3$, 16α,β (1:2.4)).

MS (m/e): 594 (M$^+$), 504 (M$^+$−C$_7$H$_6$).

Exact mass: calculated for $C_{36}H_{51}O_2Br=594.3045$ found=594.3072.

Step D. Synthesis of 16β-(11'-bromoundecanyl)-1,3,5(10)-estratrien-3,17β-diol (11, p=9)

A stirred suspension of 3-benzyloxy-16β-(11'-bromoundecanyl)-1,3,5(10)-estratrien-17β-ol (step C, 300 mg, 0,50 mmol) and 10% Pd/C (150 mg) in dry THF (4 mL) was stirred under hydrogen atmospheric pressure for 3–6 h. The reaction was followed by TLC until completion. The insoluble material was filtered off with diethyl ether (70 mL) and the filtrate was concentrated to give the crude product. It was purified by flash chromatography (hexanes:acetone (4:1)) to give 225 mg (90%) of a white solid.

IR (NaCl, $v_{max}$, cm$^{-1}$): 3600–3100 (O—H), 1604 (C=C), 1247 and 1068 (C—O).

$^1$H-NMR (CDCl$_3$, δ ppm): 7.15 (1H, d, J=8.5 Hz, 1-CH), 6.62 (1H, d, J=8.7 Hz, 2-CH), 6.56 (1H, s, 4-CH), 4.75–4.35 (1H, br s, 3-OH), 3.73 (1H, d, J=10.1 Hz, CHOH, 16β), 3.41 (2H, t, J=6.8 Hz, CH$_2$Br), 3.27 (1H, d, J=7.6 Hz, CHOH, 16α), 2.82 (2H, m, 6-CH$_2$), 2.30–0.97 (33H, #m, 4×CH, 14×CH$_2$, 17-OH), 0.80 and 0.77 (3H, 2s, 18-CH$_3$, 16α,β (1:3.9)).

$^{13}$C-NMR (CDCl$_3$, δ ppm), major 16β isomer: 153.5 (3-C), 138.1 (5-C), 132.5 (10-C), 126.4 (1-C), 115.2 (4-C), 112.7 (2-C), 82.4 (CHOH, 16β), 48.5, 44.1, 44.0, 39.9, 38.3, 37.6, 34.0, 32.8, 32.3, 31.4, 29.8, 29.61, 29.56, 29.5, 29.4, 28.7, 28.6, 28.1, 27.4, 26.2, 12.3 (18-C).

MS (m/e): 504 (M$^+$), 426 (M$^+$–$^{78}$Br).

Exact mass: calculated for $C_{29}H_{45}O_2Br=504.2592$ found=504.2603.

Step E. Synthesis of 16β-[11'-(2"-pyridylethylamino)undecanyl]-1,3,5(10)-estratrien-3,17β-diol (precursor of derivative 12, o=2, p=9)

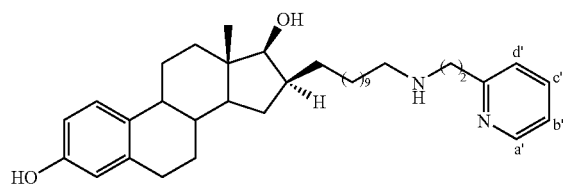

A stirred solution of bromide 11 (0.15 g, 0.30 mmol) and 2-(2-aminoethyl)pyridine (0.36 mL, 3 mmol), in methanol (5 mL) was heated to reflux for 3 days under an inert atmosphere of nitrogen. Then, the solvent was evaporated and the residue dissolved in diethyl ether (30 mL) was washed with water (5×50 mL). The aqueous phases are extracted with diethyl ether (2×15 mL). The combined organic phase were dried, filtered and evaporated to an oil. The crude amine was obtained in 80% yield and was used without further purification at the next step.

IR (NaCl, $v_{max}$, cm$^{-1}$): 3550–3050 (O—H and N—H), 1588 (C=C), 1241 and 1072 (C—O).

$^1$H-NMR (CDCl$_3$, δ ppm) 8.48 (1H, d, J=4.2 Hz, a'-CH), 7.63 (1H, t, J=7.7 Hz, c'-CH), 7.18 (2H, m, d'-CH and b'-CH), 7.12 (1H, d, J=8.2 Hz, 1-CH), 6.63 (1H, d, J=8.3 Hz, 2-CH), 6.57 (1H, s, 4-CH), 3.73 (1H, d, J=10.0 Hz, CHOH, 16β), 3.26 (1H, d, J=7.2 Hz, CHOH, 16α), 3.16 (4H, m, NHCH$_2$CH$_2$pyridyl), 2.79 (4H, m, (CH$_2$)$_{10}$CH$_2$NH and 6-CH$_2$), 2.29–1.00 (35H, m, 4×CH, 14×CH$_2$, 2×OH and NH), 0.80 and 0.76 (3H, 2s, 18-CH$_3$, 16α,β (1:4)).

$^{13}$C-NMR (CDCl$_3$, δ ppm), major 16β: 159.4 (pyridyl-C), 154.0 (3-C), 148.8 (a'-C), 138.1 (5-C), 137.0 (c'-C), 132.2 (10-C), 126.4 (1-C), 123.6 (d'-C), 121.9 (b'-C), 115.4 (4-C), 112.9 (2-C), 82.5 (CHOH, 16β), 48.8, 48.6, 48.2, 44.1, 44.0, 40.0, 38.4, 37.7, 32.4, 31.4, 29.8, 29.7, 29.6, 29.5, 29.2, 28.6, 28.3, 27.5, 27.0, 26.3, 12.4 (18-C).

MS (m/e): 546 (M$^+$), 454 (M$^+$–C$_6$H$_4$N).

Exact mass: calculated for $C_{36}H_{54}O_2N_2=546.4198$ found=546.4185.

Step F. Synthesis of 16β-[11'-(2"-pyridylethylamino)undecanyl]-1,3,5(10)-estratrien-3,17β-diol dichloroplatinate (II) (12, o=2, p=9)

To a solution of 16,8-[11'-(2"-pyridylethylamino)undecanyl]-1,3,5(10)-estratrien-3,17β-diol (step E, 0.13 g, 0.24 mmol) in DMF (1 mL) at 23° C. was added potassium tetrachloroplatinate (II) (0.11 g, 0.26 mmol) dissolved in a mixture of DMF/H$_2$O (2: 1.6 ml). The resulting mixture (pH=8–9) was stirred in the dark for 2–3 days until the pH value reached 4–5. Then, a drop of dimethylsulfoxide was added and the stirring was continued for 2–3 h. The solvent was evaporated and the residue was stirred vigorously in a saturated aqueous potassium chloride solution (5 mL) for 15 min. A vigorous stirring was essential in order to pulverize the lumps of precipitated platinum (II) complex. The resulting suspension was filtered, washed with water (100 mL) and dried in a desiccator for a 1 day. The product was further purified by flash column chromatography (hexanes:acetone, 3:2) to give the title compound in the form of yellow crystals (52% yield).

IR (NaCl, $v_{max}$, cm$^{-1}$): 3600–3100 (O—H and N—H), 1610 (C=C), $^{1211}$ and 1063 (C—O).

$^1$H-NMR (Acetone-d$_6$, 310° K, δ ppm): 9.13 (1H, d, J=5.9 Hz, a'-CH), 8.02 (1H, t, J=7.8 Hz, c'-CH), 7.53 (1H, d, J=7.8 Hz, d'-CH), 7.41 (1H, t, J=6.7 Hz, b'-CH), 7.08 (1H, d, J=8.5 Hz, 1-CH), 6.59 (1H, dd, J=1.9 Hz and J=8.5 Hz, 2-CH), 6.53 (1H, s, 4-CH), 5.87 (1H, br s, NH), 3.72 (1H, d, J=9.8 Hz, CHOH, 16#), 3.66–3.61, 3.23–3.17, 3.00–2.90 and 2.90–2.80 (7H, 4m, RCH$_2$NHCH$_2$CH$_2$pyridyl and CHOH, 16α), 2.80–2.72 (2H, m, 6-CH$_2$), 2.40–1.00 (34H, #m, 4×CH, 14×CH$_2$, 2×OH), 0.81 and 0.78 (3H, 2s, 18-CH$_3$, 16α,β (1:3.8)).

$^{13}$C-NMR (Acetone-d$_6$, δ ppm), major isomer 16β: 160.5 (pyridyl-C), 156.0 (a'-C), 154.4 (3-C), 140.0 (c'-C), 138.5 (5-C), 132.3 (10-C), 127.1 (1-C), 125.5 (d'-C), 124.6 (b'-C), 116.0 (4-C), 113.7 (2-C), 82.4 (CHOH, 16β), 57.3, 49.7, 46.8, 45.1, 41.5, 40.4, 39.6, 38.8, 33.5, 32.8, 30.8, 30.7, 28.7, 28.5, 27.3, 13.2 (18-C).

Example 7

Preparation of 16β-[11'-(2"-picolylamino)undecanyl]-1,3,5(10)-estratrien-3,17β-diol dichloroplatinate (II) (12, o=1, p=9)

Step A. Synthesis of 16β-[11'-(2"-picolylamino)undecanyl]-1,3,5(10)-estratrien-3,17β-diol (precursor of derivative 12, o=1, p=9)

The title compound was made as described for the synthesis of the amine precursor of 12, o=2 (see example 6, step E). In this case the following quantities were used: bromide 11 (70 mg, 0.14 mmol), 2-(aminomethyl)pyridine (80 μL, 0.84 mmol), methanol (2 mL). The reaction mixture was heated to reflux for 21 h under an inert atmosphere of nitrogen. The extraction was done using a mixture of diethyl ether and dichloromethane (4:1, 30 mL). The crude amine was obtained quantitatively as a yellowish oil. The title amine was used without further purification in the next step.

IR (NaCl, $v_{max}$, cm$^{-1}$): 3650–3100 (O—H and N—H), 1588 (C=C), 1246 and 1072 (C—O).

$^1$H-NMR (CDCl$_3$, δ ppm): 8.56 (1H, d, J=4.9 Hz, a'-CH), 7.64 (1H, t, J=8.2 Hz, c'-CH), 7.30 (1H, d, J=7.8 Hz, d'-CH), 7.20–7.14 (2H, m, b'-CH and 1-CH), 6.61 (1H, dd, J=2.2 and J=8.7 Hz, 2-CH), 6.56 (1H, s, 4-CH), 3.93 (2H, s, CH$_2$pyridyl), 3.73 (1H, d, J=10.0 Hz, CHOH, 16β), 3.26 (1H, d, J=7.3 Hz, CHOH, 16α), 2.82 (2H, m, 6-CH$_2$), 2.67 (1H, t, J=5.5 Hz, NH), 2.60–0.86 (36H, #m, 4×CH, 15×CH$_2$, 2×OH), 0.80 and 0.77 (3H, 2s, 18-CH$_3$, 16α,β (1:4)).

MS (m/e): 532 (M$^+$), 426 (M$^+$–C$_6$H$_6$N$_2$).

Exact mass: calculated for C$_{35}$H$_{52}$O$_2$N$_2$=532.4022 found=532.4029.

Step B. Synthesis of 16β-[11'-(2''-picolylamino)undecanyl]-1,3,5(10)-estratrien-3,17β-diol dichloroplatinate (II) (12, o=1, p=9)

This platinum (II) complex was made as described for the synthesis of the complex 12, o=2 (see example 6, step F). In this case the following quantities were used: amine (step A, 63 mg, 0.12 mmol), potassium tetrachloroplatinate (II) (60 mg, 0.14 mmol), DMF: H$_2$O (2:1, 3 mL). Purification by flash chromatography with hexanes:acetone (1:1) gave the title compound in 61% yield.

IR (NaCl, $v_{max}$, cm$^{-1}$): 3600–3050 (O—H and N—H), 1609 (C=C), 1241 and 1062 (C—O).

$^1$H-NMR (CDCl$_3$+Acetone-d$_6$ (9:1), δ ppm): 9.20 (1H, d, J=5.6 Hz, a'-CH), 8.13 (1H, t, J=7.8 Hz, c'-CH), 7.84 (1H, s, 3-OH), 7.69 (1H, d, J=7.8 Hz, d'-CH), 7.45 (1H, t, J=6.7 Hz, b'-CH), 7.15 (1H, d, J=8.4 Hz, 1-CH), 6.67 (1H, d, J=8.2 Hz, 2-CH), 6.62 (1H, s, 4-CH), 6.27 (1H, br s, NH), 4.95 (1H, dd, J=6.2 Hz and J=16.5 Hz, NHCH$_x$H$_y$pyridyl), 4.28 (1H, d, J=16.3 Hz, NHCH$_x$H$_y$pyridyl) 3.80 (1H, d, J=9.8 Hz, CHOH, 16β), 3.32 (1H, d, J=7.4 Hz, CHOH, 16α), 3.16 and 2.83 (2H, 2m, (CH$_2$)$_{10}$CH$_2$NH), 2.88 (2H, m, 6-CH$_2$), 2.34–1.05 (32H, #m, 3×CH, 14×CH$_2$, 17-OH), 0.88 and 0.86 (3H, 2s, 18-CH$_3$, 16α,β (1:3.7)).

$^{13}$C-NMR (CDCl$_3$+Acetone-d$_6$ (9:1), δ ppm), major isomer 16β: 161.6 (pyridyl-C), 154.0 (3-C), 147.4 (a'-C), 137.8 (5-C), 136.9 (c'-C), 130.7 (10-C), 125.4 (1-C), 123.4 (d'-C), 121.2 (b'-C), 114.4 (4-C), 112.0 (2-C), 81.1 (CHOH, 16β), 59.9, 54.8, 47.9, 43.3, 42.7, 39.6, 37.8, 37.1, 35.3, 31.7, 30.9, 30.1, 28.0, 26.8, 26.7, 25.8, 25.6, 11.7 (18-C).

Example 8

Preparation of 3-benzyloxy-16β-(hydroxymethyl)-16α-(11'-bromoundecanyl)-1,3,5(10)-estratrien-17#-ol (13, R=Bn, p=9)

A solution of derivative 5 (0.50 g, 0.77 mmol) in diethyl ether (20 mL) at 0° C., under N$_2$ was treated with lithium borohydride (0.10 g, 4.60 mmol). The reaction mixture was stirred at 0° C. for 3 h, then at room temperature (22° C.) for 24 h. Afterwards, the reaction mixture was diluted with diethyl ether (30 mL) and washed with a saturated ammonium chloride solution (2×20 mL), with hydrochloric acid 10% v/v (2×20 mL) and with water (2×20 mL). The organic phase was dried with MgSO$_4$, filtered and concentrated. The residue was purified by flash chromatography (hexanes: acetone, 9:1) to give the title compound with 48% yield.

IR (NaCl, $v_{max}$, cm$^{-1}$): 3331–3193 (O—H), 1604 (C=C), 1017 (C—O).

$^1$H-NMR (CDCl$_3$, δ ppm): 7.43 (2H, d, J=7.5 Hz, a-CH), 7.38 (2H, t, J=7.4 Hz, b-CH), 7.32 (1H, t, J=7.1 Hz, c-CH), 7.19 (1H, d, J=8.5 Hz, 1-CH), 6.78 (1H, dd, J=2.5 Hz and J=8.9 Hz, 2-CH), 6.72 (1H, d, J=1.4 Hz, 4-CH), 5.03 (2H, s, CH$_2$Ph), 3.79 and 3.50 (2H, 2d, J=11.3 Hz, CH$_d$H$_e$OH), 3.47 (1H, s, 17α-CH), 3.41 (2H, t, J=6.8 Hz, CH$_2$Br), 2.86–2.83 (2H, m, 6-CH$_2$), 2.31–1.06 (33H, #m, 2×OH, 3×CH, 14×CH$_2$), 0.88 (3H, s, 18-CH$_3$).

$^{13}$C-NMR (CDCl$_3$, δ ppm): 156.8 (3-C), 137.9 (CCH$_2$O), 137.3 (5-C), 132.9 (10-C), 128.5 (b-C), 127.8 (c-C), 127.4 (a-C), 126.2 (1-C), 114.8 (4-C), 112.3 (2-C), 90.7 (17-C), 69.9 (CH$_2$Ph), 66.9 (CH$_2$OH), 47.6, 47.0, 44.9, 43.9, 39.3, 38.0, 37.9, 34.0, 33.2, 32.8, 30.5, 29.73, 29.66, 29.5, 29.4, 28.8, 28.2, 27.4, 26.2, 24.7, 11.9 (18-C).

MS (m/e): 624 (M$^+$), 606 (M$^+$–H$_2$O), 544 (M$^+$–$^{80}$Br).

Exact mass: calculated for C$_{37}$H$_{53}$O$_3$Br=624.3178 found=624.3168.

Example 9

Preparation of 3-tetrahydropyranyloxy-16α,β-methoxycarbonyl-1,3,5(10)-estratrien-17-one (3, R=THP)

Step A. Synthesis of 3-tetrahydropyranyloxy-1,3,5(10)-estratrien-17-one (2, R=THP)

To a solution of estrone 1 (5.00 g, 18.62 mmol) in dichloromethane (50 mL) was added dihydropyran (5.1 mL, 55.85 mmol) and pyridinium p-toluenesulfonate (100 mg). The reaction mixture was stirred at 23° C. for 18 h. Afterwards, sodium bicarbonate (NaHCO$_3$, 500 mg) and MgSO$_4$ (5.0 g) were added to the reaction mixture and stirred 15 minutes before being filtered on a short pad of celite/silica gel (1 cm/4 cm) using DCM as the eluent. The filtrate was evaporated to a viscous oil (100% yield), which was used without further purification in the next step.

IR (KBr, $v_{max}$, cm$^{-1}$): 1742 (C=O).

$^1$H-NMR (200 MHz, CDCl$_3$, δ ppm): 7.19 (1H, d, J=8.5 Hz, 1-CH), 6.90–6.76 (2H, m, 2-CH and 4-CH), 5.39 (1H, t, J=3.50 Hz, —CH$_2$OCHO), 3.90–3.58 (2H, m, —CH$_2$OCHO), 2.88 (2H, m, 6-CH$_2$), 2.60–1.30 (19H, #m, 3×CH and 8×CH$_2$), 0.90 (3H, s, 18-CH$_3$).

$^{13}$C-NMR (200 MHz, CDCl$_3$, δ ppm): 220.9 (17-C), 155.3 (3-C), 137.9, 133.2, 132.2, 126.4, 116.8, 114.4 (4-C), 96.6, 62.2 (CH$_2$Ph), 50.7 48.2, 44.3, 38.6, 36.1, 31.8, 30.7, 29.8, 26.8, 26.1, 25.2, 21.8, 19.0, 14.1 (C-18).

Step B. Synthesis of 3-tetrahydropyranyloxy-16α,β-methoxycarbonyl-1,3,5(10)-estratrien-17-one (3, R=THP)

A solution of 3-tetrahydropyranyloxy-1,3,5(10)-estratrien-17-one (2, R=THP) (6.58 g, 18.2 mmol) in dry THF (50 mL) was added over a period of 20 min to a solution of dimethylcarbonate (3.98 mL, 47.23 mmol) and potassium hydride (2.27 g (3.6 g, 70% in oil), 56.68 mmol) in dry THF (40 mL). Then, the mixture was heated to reflux for a period of 3 h. Most of the solvent was then evaporated and the residue was diluted with ethyl acetate (100 mL) and treated with a saturated ammonium chloride solution (50 mL). The organic phase was washed with water (6×40 mL), dried and evaporated to give a yellowish solid. Trituration of the residue with a mixture of acetone:hexanes (1:1) yielded the title compound in 90% yield as a white solid.

IR (NaCl, $v_{max}$, cm$^{-1}$): 1755 (C=O, ester), 1728 (C=O, ketone).

$^1$H-NMR (200 MHz, CDCl$_3$, δ ppm): 7.19 (1H, d, J=8.5 Hz, 1-CH), 6.90–6.76 (2H, m, 2-CH and 4-CH), 5.39 (1H, t, J=3.50 Hz, —CH$_2$OCHO), 3.90–3.58 (2H, m, —CH$_2$OCHO), 3.76 (3H, s, COOCH$_3$), 3.21 (1H, t, J=8.6 Hz, 16-CH), 2.88 (2H, m, 6-CH$_2$), 2.50–1.20 (19H, #m, 3×CH and 8×CH$_2$), 0.98 (3H, s, 18-CH$_3$).

Example 10

Preparation of 3-tetrahydropyranyloxy-16β-methoxycarbonyl-16α-(bromoalkyl)-1,3,5(10)-estratrien-17-one (5, R=THP, p=2, 4, 6 or 8)

A mixture of β-cetoester 3 (R=THP, 0.15 g, 0.36 mmol), α,ω-dibromoalkane (1.80 mmol), benzyltriethylammonium chloride (50 mg), sodium hydroxide 10% w/v (3 mL), and dichloromethane (5 mL), was heated to reflux for 20 h. Afterwards, the reaction mixture was diluted with diethyl ether (40 mL) and washed with a saturated ammonium chloride solution (2×20 mL) and with water (4×50 mL). The organic phase was dried, filtered and concentrated to an oil. Flash chromatography with a mixture of hexanes:acetone (9:1) gave the desired material (5, R=THP) as an oil with good yield (65–85%). The 16α-bromoalkyl side chain were obtained stereospecifically.

3-tetrahydropyranyloxy-16β-methoxycarbonyl-16α-(4'-bromobutyl)-1,3,5(10)-estratrien-17-one (5, R=THP, p=2)

IR (NaCl, $\nu_{max}$, cm$^{-1}$): 1754 (C=O, ester), 1721 (C=O, ketone).

$^1$H-NMR (200 MHz, CDCl$_3$, δ ppm): 7.18 (1H, d, J=8.5 Hz, 1-CH), 6.85 (1H, dd, J=1.6 Hz and J=8.5 Hz, 2-CH), 6.80 (1H, d, J=1.6 Hz, 4-CH), 5.39 (1H, t, J=3.1 Hz, CH$_2$OCHO), 3.91 and 3.60 (2H, m, CH$_2$OCHO), 3.73 (3H, s, COOCH3), 3.40 (2H, t, J=6.7 Hz, CH$_2$Br), 2.88 (2H, m, 6-CH$_2$), 2.45–1.20 (23H, #m, 3×CH, 10×CH$_2$), 0.94 (3H, s, 18-CH$_3$).

$^{13}$C-NMR (200 MHz, CDCl$_3$, δ ppm): 214.0 (17-C), 171.8 (COOCH$_3$), 155.4, 137.8, 132.9, 126.4, 116.8, 114.4, 96.6, 62.1, 60.2, 52.8, 49.7, 46.3, 44.3, 38.1, 34.5, 33.3, 32.8, 32.4, 30.8, 30.6, 29.7, 26.8, 25.9, 25.5, 24.2, 19.0, 14.3 (18-C).

3-tetrahydropyranyloxy-16β-methoxycarbonyl-16α-(6'-bromohexyl)-1,3,5(10)-estratrien-17-one (5, R=THP, p=4)

IR (NaCl, $\nu_{max}$, cm$^{-1}$): 1754 (C=O, ester), 1721 (C=O, ketone).

$^1$H-NMR (CDCl$_3$, δ ppm): 7.18 (1H, d, J=8.5 Hz, 1-CH), 6.85 (1H, dd, J=1.6 Hz and J=8.5 Hz, 2-CH), 6.80 (1H, d, J=1.6 Hz, 4-CH), 5.39 (1H, br s, CH$_2$OCHO), 3.91 and 3.60 (2H, m, CH$_2$OCHO), 3.73 (3H, s, COOCH$_3$), 3.39 (2H, t, J=6.7 Hz, CH$_2$Br), 2.89 (2H, m, 6-CH$_2$), 2.45–1.20 (27H, #m, 3×CH, 12×CH$_2$), 0.93 (3H, s, 18-CH$_3$).

$^{13}$C-NMR (CDCl$_3$, δ ppm): 214.9 (17-C), 172.8 (COOCH$_3$), 156.0, 138.5, 133.7, 127.1, 117.6, 117.4, 115.0, 97.3, 62.9, 61.0, 53.5, 50.4, 47.0, 45.0, 38.8, 36.3, 34.7, 33.6, 33.0, 31.6, 31.3, 30.5, 29.8, 28.8, 27.5, 26.6, 26.2, 26.1, 19.7, 15.0 (18-C).

3-tetrahydropyranyloxy-16β-methoxycarbonyl-16α-(8'-bromooctyl)-1,3,5(10)-estratrien-17-one (5, R=THP, p=6)

IR (NaCl, $\nu_{max}$, cm$^{-1}$): 1751 (C=O, ester), 1724 (C=O, ketone).

$^1$H-NMR (CDCl$_3$, δ ppm): 7.18 (1H, d, J=8.5 Hz, 1-CH), 6.85 (1H, d, J=8.5 Hz, 2-CH), 6.80 (1H, br s, 4-CH), 5.39 (1H, br s, CH$_2$OCHO), 3.91 and 3.60 (2H, m, CH$_2$OCHO), 3.72 (3H, s, COOCH$_3$), 3.39 (2H, t, J=6.7 Hz, CH$_2$Br), 2.89 (2H, m, 6-CH$_2$), 2.45–1.20 (31H, #m, 3×CH, 14×CH$_2$), 0.92 (3H, s, 18-CH$_3$).

$^{13}$C-NMR (CDCl$_3$, δ ppm): 215.0 (17-C), 172.8 (COOCH$_3$), 156.4, 138.5, 133.7, 127.1, 117.6, 117.4, 115.0, 97.3, 62.9, 61.0, 53.5, 50.4, 47.0, 45.0, 38.8, 36.5, 34.9, 33.7, 33.0, 31.5, 31.3, 30.6, 30.5, 30.0, 29.5, 29.0, 27.5, 26.6, 26.7, 26.2, 19.7, 15.0 (18-C).

3-tetrahydropyranyloxy-16β-methoxycarbonyl-16α-(10'-bromodecanyl)-1,3,5(10)-estratrien-17-one (5, R=THP, p=8)

IR (NaCl, $\nu_{max}$, cm$^{-1}$): 1754 (C=O, ester), 1724 (C=O, ketone).

$^1$H-NMR (200 MHz, CDCl$_3$, δ ppm): 7.18 (1H, d, J=8.5 Hz, 1-CH), 6.85 (1H, dd, J=1.6 Hz and J=8.5 Hz, 2-CH), 6.80 (1H, d, J=1.6 Hz, 4-CH), 5.39 (1H, t, J=3.1 Hz, CH$_2$OCHO), 3.91 and 3.60 (2H, m, CH$_2$OCHO), 3.72 (3H, s, COOCH$_3$), 3.40 (2H, t, J=6.7 Hz, CH$_2$Br), 2.88 (2H, m, 6-CH$_2$), 2.45–1.20 (35H, #m, 3×CH, 16×CH$_2$), 0.92 (3H, s, 18-CH$_3$).

Example 11

Preparation of 16β-hydroxymethyl-16α-(bromoalkyl)-1,3,5(10)-estratrien-3,17β-diol (13, R=H, p=2, 4, 6 or 8)

A solution of derivative 5 (R=THP, 315 mg, 0.54 mmol) in diethyl ether (6 mL) at 0° C., under N$_2$ was treated with lithium borohydride (71.4 mg, 3.27 mmol). The reaction mixture was stirred at 0° C. for 3 h, then at room temperature (22° C.) for 10 h. Afterwards, the reaction mixture was treated with sodium sulfate decahydrate, stirred for 5 min and diluted with diethyl ether (30 mL). The ethereal phase was washed with a saturated ammonium chloride solution (2×20 mL) and with water (4×20 mL). The organic phase was dried with MgSO$_4$, filtered and concentrated. The crude residue (282 mg, 94%) was immediately dissolved in ethanol (4 mL) and treated with PPTs (10 mg). The resulting mixture was heated to reflux for 6 h. Then, the ethanol was evaporated and the residue dissolved in ethyl acetate was washed thoroughly with water. The organic phase was dried with MgSO$_4$, filtered and concentrated. The final compound was purified by flash chromatography (hexanes:acetone, 4:1) to give the title compound with good yield (52–65% overall).

16β-hydroxymethyl-16α-(4'-bromobutyl)-1,3,5(10)-estratrien-3,17β-diol (13, R=H, p=2)

IR (NaCl, $\nu_{max}$, cm$^{-1}$): 3355 (OH).

$^1$H-NMR (200 MHz, Acetone-d$_6$, δ ppm): 7.98 (1H, br s, OH), 7.08 (1H, d, J=8.6 Hz, 1-CH), 6.58 (1H, dd, J=2.7 Hz and J=8.6 Hz, 2-CH), 6.51 (1H, d, J=2.7 Hz, 4-CH), 4.33 (1H, d, J=4.3 Hz, CHOH), 3.80–3.30 (4H, m, OH, CH$_2$OH), 3.50 (2H, t, J=7.0 Hz, CH$_2$Br), 2.76 (2H, m, 6-CH$_2$), 2.40–1.10 (17H, #m, 3×CH, 7×CH$_2$), 0.89 (3H, s, 18-CH$_3$).

$^{13}$C-NMR (Acetone-d$_6$, δ ppm): 156.0, 138.4, 132.1, 126.9, 116.0, 113.6, 90.6, 67.2, 48.5, 47.6, 45.8, 44.9, 40.2, 39.2, 38.9, 34.8, 33.7, 30.5, 30.2, 28.9, 28.4, 27.2, 25.1, 12.5 (18-C).

16β-hydroxymethyl-16α-(6'-bromohexyl)-1,3,5(10)-estratrien-3,17β-diol (13, R=H, p=4)

IR (NaCl, $\nu_{max}$, cm$^{-1}$): 3355 (OH).

$^1$H-NMR (200 MHz, Acetone-d$_6$, δ ppm): 7.98 (1H, br s, OH), 7.08 (1H, d, J=8.6 Hz, 1-CH), 6.58 (1H, dd, J=2.7 Hz and J=8.6 Hz, 2-CH), 6.51 (1H, d, J=2.7 Hz, 4-CH), 4.33 (1H, br d, J=2.3 Hz, CHOH), 3.80–3.30 (4H, m, OH, CH$_2$OH), 3.50 (2H, t, J=7.0 Hz, CH$_2$Br), 2.76 (2H, m, 6-CH$_2$), 2.40–1.10 (21H, #m, 3×CH, 9×CH$_2$), 0.89 (3H, s, 18-CH$_3$).

$^{13}$C-NMR (Acetone-d$_6$, δ ppm): 155.9, 138.4, 132.1, 126.9, 116.0, 113.6, 90.5, 67.1, 48.5, 47.6, 45.8, 44.8, 39.2, 38.9, 34.6, 28.3, 27.2, 24.0, 12.5 (18-C).

16β-hydroxymethyl-16α-(8'-bromooctyl)-1,3,5(10)-estratrien-3,17β-diol (13, R=H, p=6)

IR (NaCl, $\nu_{max}$, cm$^{-1}$): 3355 (OH).

$^1$H-NMR (200 MHz, Acetone-d$_6$, δ ppm): 7.98 (1H, br s, OH), 7.08 (1H, d, J=8.6 Hz, 1-CH), 6.58 (1H, dd, J=2.7 Hz and J=8.6 Hz, 2-CH), 6.51 (1H, d, J=2.7 Hz, 4-CH), 4.33

(1H, d, J=4.7 Hz, CHOH), 3.80–3.30 (4H, m, OH, CH$_2$OH), 3.48 (2H, t, J=6.7 Hz, CH$_2$Br), 2.76 (2H, m, 6-CH$_2$), 2.40–1.10 (25H, #m, 3×CH, 11×CH$_2$), 0.89 (3H, s, 18-CH$_3$).

$^{13}$C-NMR (Acetone-d$_6$, δ ppm): 155.9, 138.4, 132.2, 126.9, 116.0, 113.6, 90.6, 67.2, 48.5, 47.6, 45.8, 44.9, 40.3, 39.2, 39.0, 34.7, 34.6, 33.6, 31.3, 30.3, 28.8, 28.4, 27.2, 25.2, 12.5 (18-C).

16β-hydroxymethyl-16α-(10'-bromodecanyl)-1,3,5(10)-estratrien-3,17β-diol (13, R=H, p=8)

IR (NaCl, ν$_{max}$, cm$^{-1}$): 3355 (OH).

$^1$H-NMR (200 MHz, Acetone-d$_6$, δ ppm): 7.96 (1H, br s, OH), 7.08 (1H, d, J=8.6 Hz, 1-CH), 6.58 (1H, dd, J=2.7 Hz and J=8.2 Hz, 2-CH), 6.52 (1H, d, J=2.7 Hz, 4-CH), 4.31 (1H, d, J=4.7 Hz, CHOH), 3.80–3.30 (4H, m, OH, CH$_2$OH), 3.48 (2H, t, J=6.6 Hz, CH$_2$Br), 2.76 (2H, m, 6-CH$_2$), 2.40–1.10 (29H, #m, 3×CH, 13×CH$_2$), 0.89 (3H, s, 18-CH$_3$).

$^{13}$C-NMR (Acetone-d$_6$, δ ppm): 156.0, 138.4, 132.1, 126.9, 116.0, 113.6, 90.6, 67.3, 48.5, 47.6, 45.8, 44.9, 40.3, 39.2, 39.0, 34.7, 34.5, 33.6, 31.4, 30.3, 28.8, 28.4, 27.2, 25.3, 12.5 (18-C).

Example 12

Preparation of 16β-hydroxymethyl-16α-[n-(1-pyridin-2-yl-methylamino)-alkyl]-1,3,5(10)-estratrien-3, 17β-diol dichloroplatinum (II) (14, o=1, p=2, 4, 6 or 8)

Step A. Synthesis of 16β-hydroxymethyl-16α-[4n-(1-pyridin-2-yl-methylamino)-alkyl]-1,3,5(10)-estratrien-3,17β-diol (precursor of derivative 14, o=1, p=2, 4, 6 or 8)

A stirred solution of bromide 13, R=H, p=2, 4, 6 or 8, (0.38 mmol) and 2-(aminomethyl)pyridine (3.8 mmol), in methanol (5 mL) was heated to reflux for 3 days under an inert atmosphere of nitrogen. Then, the solvent was evaporated and the residue dissolved in diethyl ether (30 mL) was washed with water (5×50 mL). The aqueous phases are extracted with diethyl ether (2×15 mL). The combined organic phase were dried, filtered and evaporated to an oil. The crude amines were obtained in more than 90% yield and were used without further purification at the next step.

16β-hydroxymethyl-16α-[4-(1-pyridin-2-yl-methylamino)-butyl]-1,3,5(10)-estratrien-3,17β-diol (precursor of derivative 14, o=1, p=2)

IR (NaCl, ν$_{max}$, cm$^{-1}$): 3650–3100 (O—H and N—H), 1597 (C=C), 758 (C—H out-of-plane, pyridine).

16β-hydroxymethyl-16α-[6-(1-pyridin-2-yl-methylamino)-hexyl]-1,3,5(10)-estratrien-3,17β-diol (precursor of derivative 14, o=1, p=4)

IR (NaCl, ν$_{max}$, cm$^{-1}$): 3650–3100 (O—H and N—H), 1594 (C=C), 758 (C—H out-of-plane, pyridine).

16β-hydroxymethyl-16α-[8-(1-pyridin-2-yl-methylamino)-octyl]-1,3,5(10)-estratrien-3,17β-diol (precursor of derivative 14, o=1, p=6)

IR (NaCl, ν$_{max}$, cm$^{-1}$): 3650–3100 (O—H and N—H), 1597 (C=C), 754 (C—H out-of-plane, pyridine).

16β-hydroxymethyl-16α-[10-(1-pyridin-2-yl-methylamino)-decyl]-1,3,5(10)-estratrien-3,17β-diol (precursor of derivative 14, o=1, p=8)

IR (NaCl, ν$_{max}$, cm$^{-1}$): 3650–3100 (O—H and N—H), 1597 (C=C), 754 (C—H out-of-plane, pyridine).

Step B. Synthesis of 16β-hydroxymethyl-16α-[n-(1-pyridin-2-yl-methylamino)-alkyl]-1,3,5(10)-estratrien-3,17β-diol dichloroplatinum (II) (14, o=1, p=2, 4, 6 or 8)

To a solution of an appropriate amino pyridine (16β-hydroxymethyl-16α-[n-(1-pyridin-2-yl-methylamino)-alkyl]-1,3,5(10)-estratrien-3,17β-diol) (step A, 0.26 mmol) in DMF (1 mL) at 23° C. was added potassium tetrachloroplatinate (II) (113 mg, 0.27 mmol) dissolved in a mixture of DMF: H$_2$O (4:1, 5 ml). The resulting mixture (pH=8–9) was stirred in the dark for 2–3 days until the pH value reached 4–5. Then, a drop of dimethylsulfoxide was added and the stirring was continued for 2–3 h. The solvent was evaporated and the residue was stirred vigorously in a saturated aqueous potassium chloride solution (5 mL) for 1 h. A vigorous stirring was essential in order to pulverize the lumps of precipitated platinum (II) complex. The resulting suspension was filtered, washed with water (100 mL) and dried in a desiccator for a day. The product was further purified by flash column chromatography (hexanes:acetone, 1:1) to give the title compounds in yields ranging from 43 to 57% for the two steps.

16β-hydroxymethyl-16α-[4-(1-pyridin-2-yl-methylamino)-butyl]-1,3,5(10)-estratrien-3,17β-diol dichloroplatinum (II) (14, o=1, p=2)

43% yield $^1$H-NMR (Acetone-d$_6$, δ ppm): 9.23 (1H, d, J=5.6 Hz, a'-CH), 8.18 (1H, t, J=8.1 Hz, c'-CH), 7.96 (1H, s, OH), 7.74 (1H, d, J=7.6 Hz, d'-CH), 7.52 (1H, t, J=6.9 Hz, b'-CH), 7.08 (1H, d, J=8.3 Hz, 1-CH), 6.58 (1H, d, J=8.3 Hz, 2-CH), 6.52 (1H, s, 4-CH), 6.14 (1H, br s, NH), 4.65 (1H, dd, J=6.6 Hz and J=16.8 Hz, NHCH$_x$H$_y$pyridyl), 4.34 (1H, d, J=17.0 Hz, NHCH$_x$H$_y$pyridyl), 4.29 (1H, t, J=5.4 Hz, CH$_2$OH), 3.72, 3.56, 3.45, 3.40, 3.07 and 2.96 (6H, 6m, RCH$_2$NHCH$_2$pyridyl, CHOH and CH$_2$OH), 2.75 (2H, m, 6-CH$_2$), 2.35–1.05 (17H, #m, 3×CH, 7×CH$_2$), 0.87 (3H, s, 18-CH$_3$).

16β-hydroxymethyl-16α-[6-(1-pyridin-2-yl-methylamino)-hexyl]-1,3,5(10)-estratrien-3,17β-diol dichloroplatinum (II) (14, o=1, p=4)

57% yield $^1$H-NMR (Acetone-d$_6$, CDCl$_3$ (9:1), δ ppm): 9.16 (1H, d, J=5.5 Hz, a'-CH), 8.03 (1H, t, J=7.6 Hz, c'-CH), 7.56 (1H, d, J=7.6 Hz, d'-CH), 7.26 (1H, s, OH), 7.35 (1H, t, J=6.3 Hz, b'-CH), 7.11 (1H, d, J=8.5 Hz, 1-CH), 6.64 (1H, d, J=8.3 Hz, 2-CH), 6.57 (1H, s, 4-CH), 6.12 (1H, br s, NH), 4.86 (1H, dd, J=6.7 Hz and J=15.4 Hz, NHCH$_x$H$_y$pyridyl), 4.13 (1H, d, J=15.4 Hz, NHCH$_x$H$_y$pyridyl), 3.91 (1H, br s, CH$_2$OH), 3.78, 3.53, 3.46, 3.10 and 2.97 (6H, 5m, RCH$_2$NHCH$_2$pyridyl, CHOH and CH$_2$OH), 2.76 (2H, m, 6-CH$_2$), 2.35–1.05 (21H, #m, 3×CH, 9×CH$_2$), 0.88 (3H, s, 18-CH$_3$).

16β-hydroxymethyl-16α-[8-(1-pyridin-2-yl-methylamino)-octyl]-1,3,5(10)-estratrien-3,17β-diol dichloroplatinum (II) (14, o=1, p=6)

48% yield $^1$H-NMR (Acetone-d$_6$, δ ppm): 9.23 (1H, d, J=8.5 Hz, a'-CH), 8.17 (1H, t, J=8.1 Hz, c'-CH), 8.00 (1H, s, OH), 7.70 (1H, d, J=7.6 Hz, d'-CH), 7.50 (1H, t, J=6.9 Hz, b'-CH), 7.08 (1H, d, J=8.3 Hz, 1-CH), 6.58 (1H, d, J=8.3 Hz, 2-CH), 6.52 (1H, s, 4-CH), 6.01 (1H, br s, NH), 4.63 (1H, dd, J=6.6 Hz and J=16.7 Hz, NHCH$_x$H$_y$pyridyl), 4.32 (1H, d, J=16.7 Hz, NHCH$_x$H$_y$pyridyl), 4.21 (1H, t, J=5.4 Hz, CH$_2$OH), 3.70, 3.50, 3.42, 3.07 and 2.92 (6H, 5m, RCH$_2$NHCH$_2$pyridyl, CHOH and CH$_2$OH), 2.75 (2H, m, 6-CH$_2$), 2.35–1.10 (25H, #m, 3×CH, 11×CH$_2$), 0.88 (3H, s, 18-CH$_3$).

16β-hydroxymethyl-16α-[10-(1-pyridin-2-yl-methylamino)-decyl]-1,3,5(10)-estratrien-3,17β-diol dichloroplatinum (II) (14, o=1, p=8)

54% yield $^1$H-NMR (Acetone-d$_6$, δ ppm): 9.23 (1H, d, J=5.5 Hz, a'-CH), 8.17 (1H, t, J=7.5 Hz, c'-CH), 7.87 (1H, s, OH), 7.71 (1H, d, J=7.6 Hz, d'-CH), 7.49 (1H, t, J=6.6 Hz, b'-CH), 7.08

(1H, d, J=8.3 Hz, 1-CH), 6.58 (1H, d, J=8.3 Hz, 2-CH), 6.52 (1H, s, 4-CH), 6.03 (1H, br s, NH), 4.63 (1H, dd, J=6.0 Hz and J=16.4 Hz, NHCH$_x$H$_y$pyridyl), 4.32 (1H, d, J=16.4 Hz, NHCH$_x$H$_y$pyridyl), 4.22 (1H, t, J=4.2 Hz, CH$_2$OH), 3.71, 3.51, 3.45, 3.05 and 2.92 (6H, 5m, RCH$_2$NHCH$_2$pyridyl, CHOH and CH$_2$OH), 2.75 (2H, m, 6-CH$_2$), 2.35–1.05 (29H, #m, 3×CH, 13×CH$_2$), 0.89 (3H, s, 18-CH$_3$).

Example 13

Preparation of 16β-hydroxymethyl-16α-[n-(2-pyridin-2-yl-ethylamino)-alkyl]-1,3,5(10)-estratrien-3, 17β-diol dichloroplatinum (II) (14, o=2, p=2, 4, 6 or 8)

Step A. Synthesis of 16β-hydroxymethyl-16α-[n-(2-pyridin-2-yl-ethylamino)-alkyl]-1,3,5(10)-estratrien-3,17β-diol (precursor of derivative 14, o=2, p=2, 4, 6 or 8)

The amines were made as described for the synthesis of the amine precursor of 14, o=1 (see example 12, step A). In this case the following quantities were used bromide 13, R=H, p=2, 4, 6 or 8 (0.50 mmol), 2-(2-aminoethyl)pyridine (5.0 mmol), methanol (5 mL). The reaction mixture was heated to reflux for 24 h under an inert atmosphere of nitrogen. The extraction was done using a mixture of diethyl ether and dichloromethane (4:1, 30 mL). The crude amines were obtained in more than 85% yield and were used without further purification at the next step.

16β-hydroxymethyl-16α-[4-(2-pyridin-2-yl-ethylamino)-butyl]-1,3,5(10)-estratrien-3,17β-diol (precursor of derivative 14, o=2, p=2)
IR (NaCl, $\nu_{max}$, cm$^{-1}$): 3650–3100 (O—H and N—H), 1597 (C=C), 758 (C—H out-of-plane, pyridine).

16β-hydroxymethyl-16α-[6-(2-pyridin-2-yl-ethylamino)-hexyl]-1,3,5(10)-estratrien-3,17β-diol (precursor of derivative 14, o=2, p=4)
IR (NaCl, $\nu_{max}$, cm$^{-1}$): 3650–3100 (O—H and N—H), 1597 (C=C), 758 (C—H out-of-plane, pyridine).

16β-hydroxymethyl-16α-[10-(2-pyridin-2-yl-ethylamino)-octyl]-1,3,5(10)-estratrien-3,17β-diol (precursor of derivative 14, o=2, p=6)
IR (NaCl, $\nu_{max}$, cm$^{-1}$): 3650–3100 (O—H and N—H), 1594 (C=C), 754 (C—H out-of-plane, pyridine).

16β-hydroxymethyl-16α-[10-(2-pyridin-2-yl-ethylamino)-decyl]-1,3,5(10)-estratrien-3,17β-diol (precursor of derivative 14, o=2, p=8)
IR (NaCl, $\nu_{max}$, cm$^{-1}$): 3650–3100 (O—H and N—H), 1597 (C=C), 758 (C—H out-of-plane, pyridine).

Step B. Synthesis of 16β-hydroxymethyl-16α-[n-(2-pyridin-2-yl-ethylamino)-alkyl]-1,3,5(10)-estratrien-3,17β-diol dichloroplatinum (II) (14, o=2, p=2, 4, 6 or 8)

These platinum (II) complexes were made as described for the synthesis of the platinum (II) complexes 14, o=1 (see example 12, step B). In these cases, the following quantities were used: an appropriate amino pyridine (16β-hydroxymethyl-16α-[n-(2-pyridin-2-yl-ethylamino)-alkyl]-1,3,5(10)-estratrien-3,17β-diol) (step A, 0.26 mmol), potassium tetrachloroplatinate (II) (113 mg, 0.27 mmol), DMF: H$_2$O (4:1, 5 mL). Purification by flash chromatography with hexanes: acetone (1:1) gave the title compounds in yields ranging from 40 to 59% for the two steps.

16β-hydroxymethyl-16α-[4-(2-pyridin-2-yl-ethylamino)-butyl]-1,3,5(10)-estratrien-3,17β-diol dichloroplatinum (II) (14, o=2, p=2)
47% yield
$^1$H-NMR (Acetone-d$_6$, δ ppm): 9.12 (1H, d, J=5.5 Hz, a'-CH), 8.04 (1H, t, J=7.3 Hz, c'-CH), 7.97 (1H, s, OH), 7.53 (1H, d, J=7.5 Hz, d'-CH), 7.43 (1H, t, J=6.5 Hz, b'-CH), 7.08 (1H, d, J=8.6 Hz, 1-CH), 6.59 (1H, dd, J=1.3 Hz and J=8.6 Hz, 2-CH), 6.51 (1H, s, 4-CH), 5.92 (1H, br s, NH), 4.28 (1H, t, J=5.2 Hz, CH$_2$OH), 3.72, 3.61, 3.45, 3.20 and 2.90 (10H, 5m, RCH$_2$NHCH$_2$CH$_2$pyridyl, CHOH and CH$_2$OH), 2.74 (2H, m, 6-CH$_2$), 2.45–1.00 (17H, #m, 3×CH, 7×CH$_2$), 0.87 (3H, s, 18-CH$_3$).

16β-hydroxymethyl-16α-[6-(2-pyridin-2-yl-ethylamino)-hexyl]-1,3,5(10)-estratrien-3,17β-diol dichloroplatinum (II) (14, o=2, p=4)
40% yield
$^1$H-NMR (Acetone-d$_6$, δ ppm): 9.13 (1H, d, J=5.5 Hz, a'-CH), 8.03 (1H, t, J=7.5 Hz, c'-CH), 7.98 (1H, s, OH), 7.53 (1H, d, J=7.5 Hz, d'-CH), 7.43 (1H, t, J=6.5 Hz, b'-CH), 7.08 (1H, d, J=8.4 Hz, 1-CH), 6.59 (1H, dd, J=1.3 Hz and J=8.3 Hz, 2-CH), 6.53 (1H, s, 4-CH), 6.08 (1H, br s, NH), 4.31 (1H, t, J=3.3 Hz, CH$_2$OH), 3.72, 3.61, 3.45, 3.20 and 2.90 (10H, 5m, RCH$_2$NHCH$_2$CH$_2$pyridyl, CHOH and CH$_2$OH), 2.75 (2H, m, 6-CH$_2$), 2.40–1.00 (21H, #m, 3×CH, 9×CH$_2$), 0.87 (3H, s, 18-CH$_3$).
$^{13}$C-NMR (Acetone-d$_6$, δ ppm): 160.5 (pyridyl-C), 155.9 (a'-C), 154.4 (3-C), 140.1 (c'-C), 138.4 (5-C), 132.1 (10-C), 127.0 (1-C), 125.6 (d'-C), 124.6 (b'-C), 116.0 (4-C), 113.6 (2-C), 90.5 (CHOH), 67.2, 57.2, 48.4, 47.5, 46.6, 45.8, 44.8, 40.5, 40.2, 39.2, 38.9, 34.7, 30.9, 30.9, 30.7, 28.5, 28.4, 27.2, 25.1, 12.6 (18-C).

16β-hydroxymethyl-16α-[8'-(2-pyridin-2-yl-ethylamino)-octyl]-1,3,5(10)-estratrien-3,17β-diol dichloroplatinum (II) (14, o=2, p=6)
44% yield
$^1$H-NMR (Acetone-d$_6$, δ ppm): 9.12 (1H, d, J=5.5 Hz, a'-CH), 8.03 (1H, t, J=7.3 Hz, c'-CH), 7.87 (1H, s, OH), 7.53 (1H, d, J=7.7 Hz, d'-CH), 7.42 (1H, t, J=6.5 Hz, b'-CH), 7.09 (1H, d, J=8.3 Hz, 1-CH), 6.59 (1H, d, J=8.3 Hz, 2-CH), 6.52 (1H, s, 4-CH), 5.83 (1H, br s, NH), 4.22 (1H, s, CH$_2$OH), 3.70, 3.45, 3.18, 2.94 and 2.87 (10H, 5m, RCH$_2$NHCH$_2$CH$_2$pyridyl, CHOH and CH$_2$OH), 2.74 (2H, m, 6-CH$_2$), 2.45–1.00 (25H, #m, 3×CH, 11×CH$_2$), 0.89 (3H, s, 18-CH$_3$).

16β-hydroxymethyl-16α-[10-(2-pyridin-2-yl-ethylamino)-decyl]-1,3,5(10)-estratrien-3,17β-diol dichloroplatinum (II) (14, o=2, p=8)
59% yield
$^1$H-NMR (Acetone-d$_6$, CDCl$_3$, δ ppm): 9.12 (1H, d, J=5.5 Hz, a'-CH), 8.03 (1H, t, J=7.3 Hz, c'-CH), 7.87 (1H, s, OH), 7.53 (1H, d, J=7.7 Hz, d'-CH), 7.42 (1H, t, J=6.5 Hz, b'-CH), 7.09 (1H, d, J=8.3 Hz, 1-CH), 6.59 (1H, d, J=8.3 Hz, 2-CH), 6.52 (1H, s, 4-CH), 5.83 (1H, br s, NH), 4.31 (1H, t, J=3.3 Hz, CH$_2$OH), 3.70, 3.45, 3.18, 2.94 and 2.87 (10H, 5m, RCH$_2$NHCH$_2$CH$_2$pyridyl, CHOH and CH$_2$OH), 2.74 (2H, m, 6-CH$_2$), 2.45–1.00 (29H, #m, 3×CH, 13×CH$_2$), 0.89 (3H, s, 18-CH$_3$)

Example 14

Preparation of 3-benzyloxy-16α,β-[111'-(2''-pyridyl-ethylamino)-3',6',9'-trioxaundecanyl]-1,3,5(10)-estratrien-17β-ol Step A. Synthesis of 3-benzyloxy-16α,β-[11'-hydroxy-3',6',9'-trioxaundecanyl)-1,3,5(10)-estratrien-17-one (15)

A solution of derivative 6 (example 3, 0.46 g, 0.68 mmol), lithium chloride (0.63 g, 14.9 mmol) and water (0.27 mL, 14.9 mmol), In DMF (8 mL) was stirred to reflux for 20 h. Afterwards, the solvent was partly evaporated and the residue was transferred to an extraction funnel with ethyl acetate 40 mL and water (50 mL). The organic phase was washed with a hydrochloric acid solution 10% v/v (2×20 mL), with water, (4×50 mL) and then dried, filtered and evaporated.

The oily residue was purified by flash chromatography (hexanes:acetone (7:3)) to give the title compound with 96% yield.

IR (NaCl, $\nu_{max}$, cm$^{-1}$): 3550–3100 (O—H), 1727 (C=O), 1604 (C=C), 1124 (C—O).

$^1$H-NMR (CDCl$_3$, δ ppm): 7.43 (2H, d, J=7.2 Hz, a-CH), 7.38 (2H, t, J=7.4 Hz, b-CH), 7.31 (1H, t, J=7.4 Hz, c-CH), 7.19 (1H, d, J=8.7 Hz, 1-CH), 6.79 (1H, dd, J=2.6 Hz and 8.5 Hz, 2-CH), 6.73 (1H, s, 4-CH), 5.03 (2H, s, CH$_2$Ph), 3.75–3.52 (14H, t, J=4.5 Hz and 2×m, 7×CH$_2$O), 2.91–2.88 (2H, m, 6-CH$_2$), 2.63–1.35 (15H, #m, OH, 4×CH, 4×CH$_2$, 16-CHCH$_2$CH$_2$O), 0.94 and 0.87 (3H, 2s, 18-CH$_3$, 16α,β (1:2)).

MS (m/e): 536 (M$^+$), 445 (M$^+$–C$_7$H$_7$), 360 (M$^+$–C$_8$H$_{16}$O$_4$).

Exact mass: calculated for C$_{33}$H$_{44}$O$_6$=536.3144; found=536.3138.

Step B. Synthesis of 3-benzyloxy-16α,β-(11'-hydroxy-3', 6',9'-trioxaundecanyl)-1,3,5(10)-estratrien-17β-ol (16)

To a solution of derivative 15 (1.15 g, 2.14 mmol) in dry THF (15 mL) at −78° C., under an inert nitrogen atmosphere, was slowly added a solution of lithium aluminum hydride 1M/THF (21.4 mL, 21.4 mmol). The resulting mixture was stirred for 1 h. Then, water (3 mL), a solution of 1N NaOH (8 mL) and once again water (8 mL) were added to destroy the excess LiAlH$_4$ and to avoid the formation of a gel. The reaction mixture was diluted with diethyl ether (40 mL), extracted with a solution of hydrochloric acid (10% v/v, 3×20 mL) and with water (5×50 mL). The organic phase was dried, filtered and evaporated to an oil (92% yield). The crude was used without further purification at the next step.

IR (NaCl, $\nu_{max}$, cm$^{-1}$): 3600–3100 (O—H), 1604 (C=C), 1124 (C—O).

$^1$H-NMR (CDCl$_3$, δ ppm): 7.42 (2H, d, J=7.4 Hz, a-CH), 7.37 (2H, t, J=7.3 Hz, b-CH), 7.31 (1H, t, J=7.0 Hz, c-CH), 7.20 (1H, d, J=8.6 Hz, 1-CH), 6.78 (1H, dd, J=2.2 Hz and 8.7 Hz, 2-CH), 6.71 (1H, s, 4-CH), 5.03 (2H, s, CH$_2$Ph), 3.78 (1H, d, J=9.1 Hz, CHOH, 16β), 3.75–3.40 (14H, t, J=4.4 Hz and #m, 7×CH$_2$O), 3.37 (1H, d, J=7.5 Hz, CHOH, 16α), 3.33 (2H, br s, CHOH and CH$_2$OH), 2.86–2.80 (2H, m, 6-CH$_2$), 2.30–1.10 (14H, #m, 4×CH, 4×CH$_2$, 16-CHCH$_2$CH$_2$O), 0.84 and 0.78 (3H, 2s, 18-CH$_3$, 16α,β (1:1.5)).

MS (m/e): 538 (M$^+$), 520 (M$^+$–H$_2$O), 447 (M$^+$–C$_7$H$_7$).

Exact mass: calculated for C$_{33}$H$_{46}$O$_6$=538.3289; found=538.3294.

Step C. Synthesis of 3-benzyloxy-16α,β-(11'-tosyloxy-3',6',9'-trioxaundecanyl)-1,3,5(10)-estratrien-17β-ol (precursor of derivative 17)

A solution of diol 16 (0.61 g, 1.10 mmol), tosyl chloride (0.24 g, 1.20 mmol) and triethylamine (0.18 mL, 1.30 mmol) in 4 mL DCM, was stirred at 0° C., under N$_2$ at for a period of 15 min and then at room temperature (22° C.) for a period of 20 h. Afterwards, the DCM was evaporated and diethyl ether (10 mL) was added to give a precipitate. The reaction mixture was filtered with diethyl ether (50 mL), evaporated and purified by flash chromatography with initially a mixture of hexanes acetone (7:3) followed by a mixture of hexanes:acetone (3:2). The title compound was obtained as an oil in 82% yield.

IR (NaCl, $\nu_{max}$, cm$^{-1}$): 3600–3150 (O—H), 1600 (C=C), 1354 (SO$_2$), 1099 (C—O).

$^1$H-NMR (CDCl$_3$, δ ppm): 7.81 (2H, d, J=8.5 Hz, d-CH), 7.43 (2H, d, J=7.3 Hz, a-CH), 7.38 (2H, t, J=7.6 Hz, b-CH), 7.35–7.30 (3H, m, c-CH and e-CH), 7.21 (1H, d, J=8.7 Hz, 1-CH), 6.78 (1H, dd, J=2.2 Hz and J=8.9 Hz, 2-CH), 6.72 (1H, s, 4-CH), 5.03 (2H, s, CH$_2$Ph), 4.17 (2H, t, J=4.7 Hz, CH$_2$OTs), 3.75 (1H, d, J=9.4 Hz, CHOH, 16β), 3.71–3.40 (12H, t, J=4.5 Hz and #m, 6×CH$_2$O), 3.32 (1H, d, J=7.5 Hz, CHOH, 16α), 2.87–2.83 (2H, m, 6-CH$_2$), 2.64 (1H, br s, CHOH), 2.45 (3H, s, CH$_3$), 2.30–1.10 (14H, #m, 4×CH, 4×CH$_2$, 16-CHCH$_2$CH$_2$O), 0.81 and 0.77 (3H, 2s, 18-CH$_3$, 16α,β (1:1.8)).

MS (m/e): 692 (M$^+$), 520 (M$^+$–C$_7$H$_8$O$_3$S).

Exact mass: calculated for C$_{40}$H$_{52}$SO$_8$=692.3370; found=692.3383.

Step D. Synthesis of 3-benzyloxy-16α,β-(11'-iodo-3',6', 9'-trioxaundecanyl)-1,3,5(10)-estratrien-17β-ol (17)

To a solution of the tosylate prepared at step C (0.63 g, 0.91 mmol) and sodium iodide (0.34 g, 2.30 mmol) in dry acetone (7 mL), was stirred at room temperature (22° C.), for 20 h under N$_2$. Then, the acetone was evaporated. The residue was transferred into an extraction funnel with diethyl ether (40 mL) was washed subsequently with a sodium thiosulfate solution (5% w/v, 10 mL) and with water (5×70 mL). The ethereal phase was dried, filtered and concentrated to an oil. The crude material was purified by flash chromatography (hexanes:acetone (6:4)) to give a colorless oil (90%)

IR (NaCl, $\nu_{max}$, cm$^{-1}$): 3600–3150 (O—H), 1602 (C=C), 1102 (C—O).

$^1$H-NMR (CDCl$_3$, δ ppm): 7.43 (2H, d, J=7.2 Hz, a-CH), 7.38 (2H, t, J=7.4 Hz, b-CH), 7.31 (1H, t, J=7.5 Hz, c-CH), 7.21 (1H, d, J=8.6 Hz, 1-CH), 6.78 (1H, dd, J=2.6 Hz and J=8.5 Hz, 2-CH), 6.71 (1H, d, J=1.4 Hz, 4-CH), 5.03 (2H, s, CH$_2$Ph), 3.77 (3H, t, J=7.1 Hz, OCH$_2$CH$_2$I and CHOH 16β), 3.68–3.40 (10H, m, 5×CH$_2$O), 3.35 (1H, d, J=7.4 Hz, CHOH, 16α), 3.28 (2H, t, J=6.9 Hz, CH$_2$I), 2.87–2.80 (2H, m, 6-CH$_2$), 2.61 (1H, br s, CHOH), 2.31–1.07 (14H, #m, 4×CH, 4×CH$_2$, 16-CHCH$_2$CH$_2$O), 0.83 and 0.78 (3H, 2s, 18-CH$_3$, 16α,β (1:1.8)).

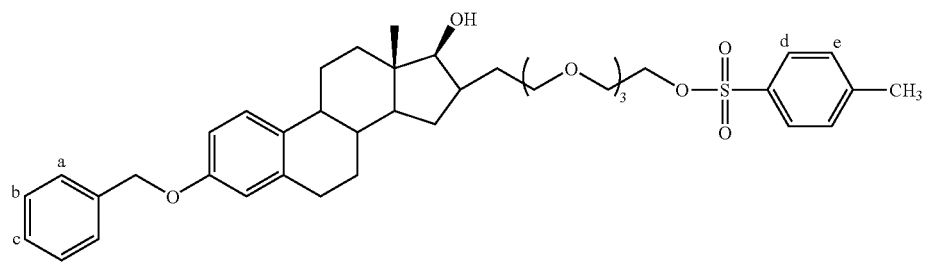

Exact mass: calculated for C$_{33}$H$_{45}$IO$_5$=648.2317; found=648.2312.

Step E. Synthesis of 3-benzyloxy-16α,β-[11'-(2''-pyridyl-ethylamino)-3',6',9'-trioxaundecanyl]-1, 3,5(10)-estratrien-17β-ol (precursor of derivative 18)

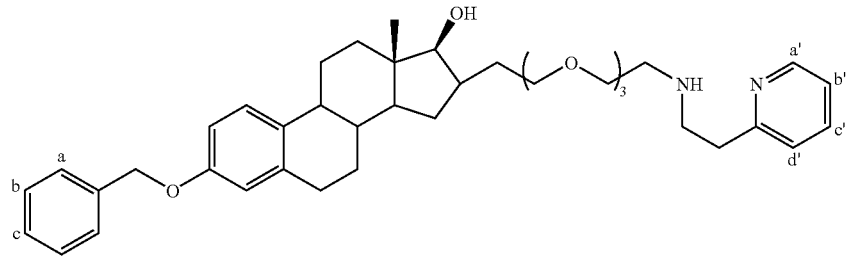

A solution of iodide 17 (0.08 g, 0.12 mmol) and 2-(2-aminoethyl)pyridine (0.15 mL, 1.20 mmol), in methanol (2 mL) was heated to a gentle reflux for a period of 48 under a N₂ atmosphere. Then, the solvent was evaporated and the residue taken up with diethyl ether (30 mL) and dichloromethane (3 mL) and washed throughroughly with water (5×50 mL). The aqueous portions were washed with diethyl ether (20 mL). The combined ethereal phases were dried with MgSO₄, filtered and concentrated to an oil. The crude amine was purified by flash chromatography with a mixture of dichloromethane:methanol:triethylamine (9:1:0.1). The amine was obtained as a yellowish oil (90%).

IR (NaCl, $v_{max}$, cm$^{-1}$): 3600–3000 (O—H and N—H), 1604 (C=C), 1098 (C—O).

$^1$H-NMR (CDCl₃, δ ppm): 8.47 (1H, d, J=4.5 Hz, a'-CH), 7.64 (1H, t, J=7.4 Hz, c'-CH), 7.41 (2H, d, J=7.4 Hz, a-CH), 7.35 (2H, t, J=7.4 Hz, b-CH), 7.29 (1H, t, J=7.2 Hz, c-CH), 7.23–7.17 (3H, m, b'-CH, d'-CH and 1-CH), 6.76 (1H, d, J=8.8 Hz, 2-CH), 6.70 (1H, s, 4-CH), 5.60–4.90 (2H, br s, NH and OH), 5.01 (2H, s, CH₂Ph), 3.85–3.38 (12H, t, J=4.3 Hz and #m, 6×CH₂O), 3.74 (1H, d, J=9.6 Hz, CHOH, 16β), 3.38–3.10 (7H, 3m, OCH₂CH₂NHCH₂CH₂pyridyl, CHOH, 16α), 2.86–2.79 (2H, m, 6-CH₂), 2.27–1.06 (14H, #m, 4×CH, 4×CH₂, 16-CHCH₂CH₂O), 0.80 and 0.75 (3H, 2s, 18-CH₃, 16α,β (1:1.6)).

MS (m/e): 642 (M⁺), 550 (M⁺–H⁺ and C₇H₇).

Exact mass calculated for C₄₀H₅₄N₂O₅=642.4032 found=642.4019.

Example 15

Preparation of 16β-hydroxymethyl-16α-[8'-(2-pyridin-2-yl-ethylamino)-3',6'-dioxaoctyl]-1,3,5(10)-estratrien-3,17β-diol dichloroplatinum (II)

Step A. Synthesis of 3-tetrahydropyranyloxy-16β-methoxycarbonyl-16α-(8'-bromo-3',6'-dioxaoctyl)-1,3,5(10)-estratrien-17-one (6, R=THP, Y'=Br)

A solution of β-cetoester 3 product of example 9 (R=THP, 3.0 g, 7.27 mmol), 1,8-dibromo-3,6-dioxaoctane (see general procedure 3 for the preparation of this compound) (12.04 g, 43.6 mmol), benzyltriethylammonium chloride (400 mg) and sodium hydroxide 10% w/v (20 mL), in 36 mL DCM, was stirred vigorously and heated to reflux for 20 h. The reaction mixture was diluted with diethyl ether (100 mL) and washed with a saturated ammonium chloride solution (2×30 mL) and with water (4×50 mL). The organic phase was filtered, dried and evaporated to an oil. The crude material was purified by flash chromatography with a mixture of hexanes:acetone (98:2) to give 1.12 g (25%) of the desired material.

IR (NaCl, $v_{max}$, cm$^{-1}$): 1751 (C=O, ester), 1721 (C=O, ketone).

$^1$H-NMR (200 MHz, CDCl₃, δ ppm): 7.15 (1H, d, J=8.6 Hz, 1-CH), 6.85 (1H, dd, J=1.6 Hz and J=8.5 Hz, 2-CH), 6.80 (1H, d, J=1.6 Hz, 4-CH), 5.37 (1H, t, J=2.7 Hz, —CH₂OCHO), 3.95 and 3.60 (2H, m, —CH₂OCHO), 3.77 (2H, t, J=6.3 Hz, CH₂CH₂OCH₂CH₂OCH₂CH₂Br), 3.70 (3H, s, COOCH₃), 3.57 (6H, m, CH₂CH₂OCH₂CH₂OCH₂CH₂Br), 3.44 (2H, t, J=6.3 Hz, CH₂Br), 2.86 (2H, m, 6-CH₂), 2.45–1.10 (19H, #m, 3×CH, 8×CH₂), 0.93 (3H, s, 18-CH₃).

$^{13}$C-NMR (CDCl₃, δ ppm): 214.0 (17-C), 172.0 (COOCH₃), 155.4, 137.7, 133.0, 126.3, 116.9, 114.4, 96.6, 71.4, 70.7, 70.4, 68.1, 62.2, 58.5, 52.8, 49.6, 46.3, 44.3, 38.1, 35.1, 32.5, 31.4, 30.7, 30.5, 29.7, 26.8, 25.9, 25.5, 19.0, 14.3 (18-C).

Step B. Synthesis of 16β-hydroxymethyl-16α-(8'-bromo-3',6'-dioxaoctyl)-1,3,5(10)-estratrien-3,17β-diol A solution of of 3-tetrahydropyranyloxy-16β-methoxycarbonyl-16α-(8'-bromo-3',6'-dioxaoctyl)-1,3,5(10)-estratrien-17-one (product of step A, 418 mg, 0.69 mmol) in diethyl ether (25 mL) at 0° C., under N₂ was treated with lithium borohydride (90 mg, 4.1 mmol). The reaction mixture was stirred at 0° C. for 3 h, then at room temperature (22° C.) for 10 h. Afterwards, the reaction mixture was treated with sodium sulfate decahydrate, stirred for 5 min and diluted with a mixture of diethyl ether and dichloromethane (3:2, 50 mL). The organic phase was washed with a saturated ammonium chloride solution (2×20 mL) and with water (4×20 mL). The organic phase was dried with MgSO₄, filtered and concentrated. The crude residue (358 mg, 89.5%) was immediately dissolved in ethanol (10 mL) and treated with PPTs (60 mg). The resulting mixture was stirred at room temperature (22° C.) for a day. Then, the ethanol was evaporated and the residue dissolved in ethyl acetate was washed thoroughly with water. The organic phase was dried with MgSO₄, filtered and concentrated. The final compound was purified by flash chromatography (hexanes:acetone, 4:1) to give 185 mg (54%) of the desired material.

IR (NaCl, $v_{max}$, cm$^{-1}$): 3650–3100 (O—H), 1604 (C=C), 1124 (C—O).

$^1$H-NMR (200 MHz, Acetone-d₆, δ ppm): 8.09 (1H, br s, OH), 7.08 (1H, d, J=8.6 Hz, 1-CH), 6.59 (1H, dd, J=2.3 Hz and J=8.6 Hz, 2-CH), 6.52 (1H, d, J=2.3 Hz, 4-CH), 4.31 (1H, d, J=3.9 Hz, CHOH), 3.80 (2H, t, J=6.3 Hz, CH₂CH₂OCH₂CH₂OCH₂CH₂Br), 3.75–3.40 (10H, m, CH₂OH, CH₂CH₂OCH₂CH₂OCH₂CH₂Br), 3.16 (2H, br s, CHOH and CH$_2$OH), 2.75 (2H, m, 6-CH$_2$), 2.40–1.10 (13H, #m, 3×CH, 5×CH$_2$), 0.87 (3H, s, 18-CH$_3$).

$^{13}$C-NMR (Acetone-d$_6$, δ ppm): 155.9, 137.7, 131.4, 126.3, 115.3, 113.0, 89.6, 71.1, 70.3, 70.2, 68.5, 66.8, 47.6, 46.2, 45.1, 44.2, 39.3, 38.5, 38.3, 35.1, 31.1, 29.6, 27.7, 26.5, 11.9 (18-C).

Step C. Synthesis of 16β-hydroxymethyl-16α-[8'-(2-pyridin-2-yl-ethylamino)-3',6'-dioxaoctyl]-1,3,5(10)-estratrien-3,17β-diol A stirred solution 16β-hydroxymethyl-16α-(8'-bromo-3',6'-dioxaoctyl)-1,3,5(10)-estratrien-3,17β-diol (product of step B, 183 mg, 0.37 mmol) and 2-(2'-aminoethyl)pyridine (0.44 mL, 3.7 mmol), in methanol (6 mL) was heated to reflux for 3 days under an inert atmosphere of nitrogen. Then, the solvent was evaporated and the residue dissolved in diethyl ether (30 mL) was washed with water (5×30 mL). The aqueous phases are extracted with diethyl ether (2×15 mL). The combined organic phase were dried, filtered and evaporated to give the title compound. The crude amine was obtained in 92% yield and was used without further purification at the next step.

IR (NaCl, ν$_{max}$, cm$^{-1}$): 3650–3100 (O—H and N—H), 1594 (C=C), 754 (C—H out-of-plane, pyridine).

Step D. Synthesis of 16β-hydroxymethyl-16α-[8'-(2-pyridin-2-yl-ethylamino)-3',6'-dioxaoctyl]-1,3,5(10)-estratrien-3,17β-diol dichloroplatinum (II) (23)

To a solution of 16]-hydroxymethyl-16α-[8'-(2-pyridin-2-yl-ethylamino)-3',6'-dioxaoctyl]-1,3,5(10)-estratrien-3,17β-diol (product of step C, 180 mg, 0.33 mmol) in DMF (2 mL) at 22° C. was added potassium tetrachloroplatinate (II) (153 mg, 0.77 mmol) dissolved in a mixture of DMF: H$_2$O (1:2, 3 ml). The resulting mixture (pH=8–9) was stirred in the dark for 2–3 days until the pH value reached 4–5. Then, a drop of dimethylsulfoxide was added and the stirring was continued for 2–3 h. The solvent was evaporated and the residue was stirred vigorously in a saturated aqueous potassium chloride solution (5 mL) for 1 h. A vigorous stirring was essential in order to pulverize the lumps of precipitated platinum (II) complex. The resulting suspension was filtered, washed with water (100 mL) and dried in a desiccator for a day. The product was further purified by flash column chromatography (hexanes: acetone, 1:1) to give 101 mg (38% yield for steps C and D) of the title compound.

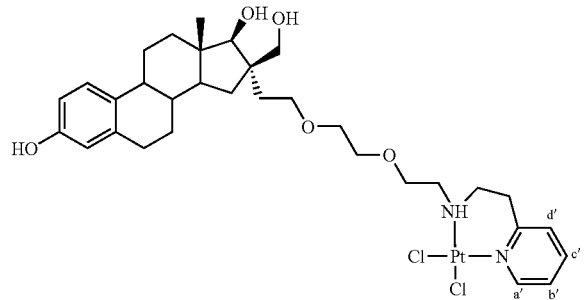

23

$^1$H-NMR (DMSO-d$_6$, δ ppm) 8.97 (1H, d, J=5.8 Hz, a'-CH), 8.95 (1H, s, OH), 8.02 (1H, t, J=7.6 Hz, c'-CH), 7.51 (1H, d, J=7.6 Hz, d'-CH), 7.41 (1H, t, J=6.6 Hz, b'-CH), 7.03 (1H, d, J=8.5 Hz, 1-CH), 6.73 (1H, br s, NH), 6.50 (1H, d, J=8.4 Hz, 2-CH), 6.53 (1H, s, 4-CH), 3.93, 3.65, 3.41 and 3.35–3.05 (17H, #m, CHOH, CH$_2$OH and CH$_2$CH$_2$OCH$_2$CH$_2$OCH$_2$CH$_2$NHCH$_2$CH$_2$pyridyl), 2.90 (2H, br s, CHOH and CH$_2$OH), 2.70 (2H, m, 6-CH$_2$), 2.40–1.10 (13H, #m, 3×CH, 5×CH$_2$), 0.73 (3H, s, 18-CH$_3$).

Example 16

Preparation of 16α,β-[10'-(N-2"-pyridylethyl)carbamoyldecanyl]-1,3,5(10)-estratrien-17-one-3-ol (21)

Step A. Synthesis of 3-benzyloxy-16α,β-(10'-carboxydecanyl)-1,3,5(10)-estratrien-17-one (19)

A solution of derivative 8 (example 5, 0.50 g, 0.81 mmol), lithium chloride (0.76 g, 17.8 mmol) and water (0.32 mL, 17.8 mmol), in DMF (6 mL) was stirred to reflux for 18 h. Afterwards, the solvent was partly evaporated and the residue was transferred to an extraction funnel with ethyl acetate 40 mL and water (50 mL). The organic phase was washed with a hydrochloric acid solution 10% v/v (2×20 mL), with water, (4×50 mL) and then dried, filtered and evaporated. The residue was purified by flash chromatography (hexanes: acetone (9:1)) to give the acid with 67% yield.

IR (NaCl, ν$_{max}$, cm$^{-1}$): 3500–3100 (O—H), 1727 (C=O, ketone), 1701 (C=O, acid), 1604 (C=C), 1022 (C—O).

$^1$H-NMR (CDCl$_3$, δ ppm): 7.43 (2H, d, J=7.5 Hz, a-CH), 7.39 (2H, t, J=7.3 Hz, b-CH), 7.32 (1H, t, J=7.1 Hz, c-CH), 7.20 (1H, d, J=8.6 Hz, 1-CH), 6.79 (1H, d, J=8.8 Hz, 2-CH), 6.74 (1H, s, 4-CH), 5.04 (2H, s, CH$_2$Ph), 2.89 (2H, m, 6-CH$_2$), 2.36 (2H, t, J=7.4 Hz, RCH$_2$COOH), 2.44–1.12 (30H, #m, 4×CH, 13×CH$_2$), 0.95 and 0.87 (3H, 2s, 18-CH$_3$, 16α,β (1:1.6)).

MS (m/e): 544 (M$^+$), 498 (M$^+$–CH$_2$O$_2$), 453 (M$^+$–C$_7$H$_7$).

Exact mass: calculated for C$_{36}$H$_{48}$O$_4$=544.3552; found=544.3559.

Step B. Synthesis of 3-benzyloxy-16α,β-[10'-(N-2"-pyridylethyl)carbamoyldecanyl]-1,3,5(10)-estratrien-17-one (20)

Oxalyl chloride (0.81 mL, 9.20 mmol) was added to the acid 19 (step A, 0.32 g, 0.59 mmol). The reaction mixture was stirred for 15 min at room temperature (22° C.), until all gas evolution ceased. Then, the excess oxalyl chloride was purged with N$_2$ gas. The resulting residue was solubilized with dichloromethane (0.5 mL) and 2-(2-aminoethyl)pyridine was added (0.56 mL, 4.70 mmol). The reaction mixture was stirred for 1 h after which time 40 mL ethyl acetate was added. The organic phase was washed with a sodium bicarbonate solution (5% w/v, 2×30 mL) and with water (4×30 mL). The organic phase was dried, evaporated and concentrate to give the crude amide. Flash chromatography with a mixture of hexanes, acetone and methanol (3:1.8:0.2) gave the desired amide with 77% yield.

IR (NaCl, ν$_{max}$, cm$^{-1}$): 3300 (N—H), 1732 (C=O, ketone), 1645 (C=O, amide), 1604 (C=C), 1022 (C—O).

$^1$H-NMR (CDCl$_3$, δ ppm): 8.52 (1H, d, J=4.0 Hz, a'-CH), 7.64 (1H, t, J=7.6 Hz, c'-CH), 7.42 (2H, d, J=7.4 Hz, a-CH), 7.37 (2H, t, J=7.3 Hz, b-CH), 7.31 (1H, t, J=7.2 Hz, c-CH), 7.18 (3H, m, d'-CH, b'-CH and 1-CH), 6.78 (1H, d, J=9.6 Hz, 2-CH), 6.73 (1H, s, 4-CH), 6.49 (1H, br s, NH), 5.03 (2H, s, CH$_2$Ph), 3.66 (2H, q, J=5.8 Hz, RNHCH$_2$CH$_2$pyridyl), 3.01 (2H, t, J=6.3 Hz, RNHCH$_2$CH$_2$pyridyl), 2.88 (2H, m, 6-CH$_2$), 2.43–1.25 (30H, #m, 4×CH, 13×CH$_2$), 2.14 (2H, t, J=7.4 Hz, RCH$_2$CONHR), 0.93 and 0.86 (3H, 2s, 18-CH$_3$, 16α,β (1:1.7)).

MS (m/e): 648 (M$^+$), 557 (M$^+$–C$_7$H$_7$).

Exact mass: calculated for C$_{43}$H$_{56}$O$_3$N$_2$=648.4291 found=648.4285.

Step C. Synthesis of 16α,β-[10'-(N-2'-pyridylethyl)carbamoyldecanyl]-1,3,5(10)-estratrien-17-one-3-ol (21)

A stirred suspension derivative 20 (step B, 130 mg, 0.20 mmol) and 10% Pd/C (50 mg) in dry THF (3 mL) was stirred under hydrogen atmospheric pressure for 36 h. The insoluble material was filtered off with diethyl ether (40 mL) and the filtrate was concentrated to give the crude product. It was purified by flash chromatography (hexanes:acetone:methanol (3:1.8:0.2)) to give 46% of the title compound.

IR (NaCl, ν$_{max}$, cm$^{-1}$): 3600–3000 (O—H), 1727 (C=O, ketone), 1650 (C=O, amide), 1600 (C=C), 1048 (C—O).

$^1$H-NMR (CDCl$_3$, δ ppm): 8.52 (1H, d, J=4.4 Hz, a'-CH), 7.66 (1H, dt, J=1.5 Hz and J=6.8 Hz, c'-CH), 7.23–7.18 (2H, m, d'-CH and b'-CH), 7.10 (1H, d, J=8.5 Hz, 1-CH), 6.67 (1H, dd, J=1.6 Hz and J=8.4 Hz, 2-CH), 6.62 (1H, d, J=1.5 Hz, 4-CH), 6.51 (1H, m, NH), 3.65 (2H, q, J=6.1 Hz, RNHCH$_2$CH$_2$pyridyl), 3.01 (2H, t, J=6.4 Hz, RNHCH$_2$CH$_2$pyridyl), 2.84 (2H, m, 6-CH$_2$), 2.43–1.23 (33H, #m, OH, 4×CH, 14×CH$_2$), 0.92 and 0.85 (3H, 2s, 18-CH$_3$, 16α,β (1:1.8)).

MS (m/e): 558 (M$^+$), 543 (M$^+$–CH$_3$).

Exact mass: calculated for C$_{36}$H$_{50}$O$_3$N$_2$=558.3821 found=558.3834.

In vitro Cytotoxic Activity of the Estradiol-linked Pt (II) Complexes

Cell Proliferation with the MTT Assay (Uterine, Ovarian and Breast Cancer Cell Lines)

Several human uterine, ovarian and breast cancer cell lines were used to evaluate the antitumor activities of the new estrogen-linked platinum (II) complexes. The cytotoxicity of the platinum (II) complexes was done along with cisplatin as the control on both ER+ and ER— human uterine, ovarian and breast carcinomas. Cell proliferation was done with the MTT assay as described by J. Carmichael et al. (Cancer Res. 47, 943–946 (1987) see also C. H. J. Ford et al., Cancer Chemother. Pharmacol. 24, 295–301 (1986)). The MTT assay is based on the ability of viable cells to reduce a soluble colorless tetrazolium salt, 3-(4,5-dimethylthiazol-2-yl)-2,5-diphenyltetrazolium bromide (MTT), into an insoluble blue formazan derivative. Table 1 presents the IC$_{50}$ obtained for derivative 12, o=1 and 12, o=2) by the MTT assay.

TABLE 1

Cell proliferation with the MTT assay on uterine carcinomas for derivatives 12.

|  | RL-95-2* (ER+) | Ishikawa* (ER+) | HEC-1A* (ER−) | KLE* (ER−) |
|---|---|---|---|---|
| Cisplatin | 14.1 ± 0.5 | 3.7 ± 0.9 | 20.8 ± 4.7 | 24.3 ± 6.3 |
| 12 (o = 1) | 7 | 28 | 13 | 6 |
| 12 (o = 2) | 1 | 0.25 | 3.75 | 1.75 |

*IC$_{50}$ (Inhibitory concentration 50%), data in μM
Average ±SEM (cisplatin)

The platinum (II) complexes 14 (o=1 or 2) and 23 were evaluated with the MTT assay on uterine, ovarian and breast cancer cell lines. The results are presented on Tables 2 and 3 below.

TABLE 2

Cell proliferation with the MTT assay on breast, ovarian and uterine carcinomas obtained for derivatives 14 (o = 1).

| Cell lines | Type | ER | 14 (o = 1, p = 2) | 14 (o = 1, p = 4) | 14 (o = 1, p = 6) | 14 (o = 1, p = 8) |
|---|---|---|---|---|---|---|
| HeLa* | Uterus | − | NR | 36.25 | 34.4 | 32.2 |
|  |  |  | (n = 2) | (n = 2) | (n = 2) | (n = 2) |
| HEC-1A | Uterus | − | NR | 19.5 | 9.2 | 15.6 |
|  |  |  | (n = 2) | (n = 2) | (n = 2) | (n = 2) |
| KLE | Uterus | − | NR | 36.25 | 19.5 | 9.5 |
|  |  |  | (n = 2) | (n = 2) | (n = 2) | (n = 2) |
| RL-95-2 | Uterus | + | 40.0 | 16 | 7.8 | 9.5 |
|  |  |  | (n = 2) | (n = 2) | (n = 2) | (n = 2) |
| Ishikawa | Uterus | + | 36.0 | NR | 19.5 | NR |
|  |  |  | (n = 2) | (n = 2) | (n = 2) | (n = 2) |
| A2780wt | Ovary | − | 33.7 | 23.5 | 6.3 | 10.0 |
|  |  |  | (n = 2) | (n = 2) | (n = 2) | (n = 2) |
| A2780cp | Ovary | − | NR | NR | 11.0 | 16.6 |
|  |  |  | (n = 2) | (n = 2) | (n = 2) | (n = 2) |
| OVCAR-3 | Ovary | + | NR | NR | 18.8 | 40.0 |
|  |  |  | (n = 2) | (n = 2) | (n = 2) | (n = 2) |
| SKOV-3 | Ovary | + | NR | NR | 35.0 | NR |
|  |  |  | (n = 2) | (n = 2) | (n = 2) | (n = 2) |
| MDA-MB-231 | Breast | − | NR | NR | 40.0 | 15.3 |
|  |  |  | (n = 2) | (n = 2) | (n = 2) | (n = 2) |
| HS578T | Breast | − | NR | 36.2 | 17.5 | 34.9 |
|  |  |  | (n = 2) | (n = 2) | (n = 2) | (n = 2) |
| MCF-7 | Breast | + | NR | NR | 20.0 | 17.7 |
|  |  |  | (n = 2) | (n = 2) | (n = 2) | (n = 2) |
| ZR-75-1 | Breast | + | NR | NR | 11.25 | 27.6 |
|  |  |  | (n = 2) | (n = 2) | (n = 2) | (n = 2) |

*IC$_{50}$ (Inhibitory concentration 50%), data in μM
NR = IC$_{50}$ not reach at the concentrations tested
n = number of experiments

TABLE 3

Cell proliferation with the MTT assay on breast, ovarian and uterine carcinomas obtained for derivatives 14 (o = 2) and derivative 23.

| Cell lines | Type | ER | 14 (o = 2, p = 2) | 14 (o = 2, p = 4) | 14 (o = 2, p = 6) | 14 (o = 2, p = 8) | 23 |
|---|---|---|---|---|---|---|---|
| HeLa | Uterus | − | 34.5 (n = 1) | 8.9 (n = 3) | 4.6 (n = 3) | 6.8 (n = 2) | 13.75 (n = 1) |
| HEC-1A | Uterus | − | 26.3 (n = 1) | 6.4 (n = 3) | 2.1 (n = 3) | 2.4 (n = 2) | 20.4 (n = 1) |
| KLE | Uterus | − | NR (n = 1) | 8.9 (n = 3) | 2.7 (n = 3) | 3.7 (n = 2) | 17.5 (n = 1) |
| RL-95-2 | Uterus | + | 10.0 (n = 1) | 6.4 (n = 3) | 0.1 (n = 3) | 3.1 (n = 2) | 6.25 (n = 1) |
| Ishikawa | Uterus | + | 16.0 (n = 1) | 20 (n = 3) | 8.0 (n = 3) | 2.2 (n = 2) | 2.5 (n = 1) |
| A2780wt | Ovary | − | 19.5 (n = 1) | 5 (n = 3) | 3.3 (n = 3) | 1.65 (n = 2) | 7.9 (n = 1) |
| A2780cp | Ovary | − | 30.5 (n = 1) | 7 (n = 3) | 3.6 (n = 3) | 2.0 (n = 3) | 16.0 (n = 1) |
| OVCAR-3 | Ovary | + | 31.2 (n = 1) | 12.5 (n = 3) | 5.0 (n = 3) | 9.5 (n = 3) | 33.75 (n = 1) |
| SKOV-3 | Ovary | + | 35.6 (n = 1) | 12.5 (n = 3) | 4.8 (n = 3) | 5.8 (n = 3) | 32.5 (n = 1) |
| MDA-MB-231 | Breast | − | NR (n = 1) | NR (n = 3) | 10.5 (n = 3) | 4.0 (n = 3) | 18.75 (n = 1) |
| HS578T | Breast | − | 33.0 (n = 1) | 7.25 (n = 3) | 4.3 (n = 3) | 3.3 (n = 3) | 16.25 (n = 1) |
| MCF-7 | Breast | + | 28.5 (n = 1) | 7 (n = 3) | 6.4 (n = 3) | 4.0 (n = 3) | 12.7 (n = 1) |
| ZR-75-1 | Breast | + | 26.3 (n = 1) | 11.4 (n = 3) | 4.6 (n = 3) | 2.5 (n = 3) | 14.6 (n = 1) |

*$IC_{50}$ (Inhibitory concentration 50%), data in μM
NR = $IC_{50}$ not reach at the concentrations tested
n = number of experiments Cell Proliferation with the SRB Assay (Breast Cancer Cell Lines)

Two human breast tumor cell lines were used to evaluate the antitumor activities of the new estrogen-linked platinum (II) complexes. The cytotoxicity of the platinum (II) complexes was done along with controls (tamoxifen and cisplatin) on both $ER^+$ (MCF-7) and $ER^-$ (MDA-MB-231) human mammary carcinomas in order to assess the potential selective antineoplastic effect on hormono-dependent breast cancer. Cell proliferation was done with the sulforhodamine B (SRB) assay as described by Alley, M. C. et al. (Cancer Research. no 48, 589–601 (1988)) and Boyd, M. R. & Paull, K. D. (Drug Development Research. 34, 91–109, (1995)). Table 4 presents the $IC_{50}$ obtained for derivative 12, o 1 and 12, o=2) by the SRB assay.

TABLE 4

Cell proliferation with the SRB assay on breast carcinomas for derivatives 12.

|  | MCF-7* (ER+) | MDA-MB-231* (ER−) |
|---|---|---|
| Cisplatin | 16.1 | 12.8 |
| Tamoxifen | 11.1 | 18.9 |
| 12 (o = 1) | 5.9 | 4.1 |
| 12 (o = 2) | <0.78 | <0.78 |

*$IC_{50}$ (Inhibitory concentration 50%), data in μM

The invention claimed is:

1. A compound of formula I

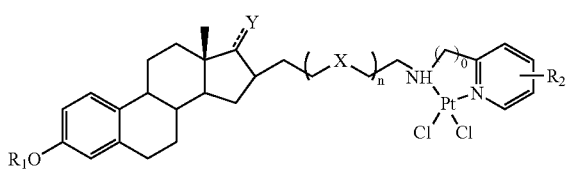

I wherein X may be —CH₂—O—CH₂— or —CH₂—, wherein n is 1, 2, 3, 4 or 5 when X is —CH₂—O—CH₂—, wherein n is 2, 3, 4, 5, 6, 7, 8, 9 or 10 when X is —CH₂—, wherein o is 1, 2 or 3, wherein Y is O or 17β-OH, where the dotted line represents the presence or absence of a second chemical bond, wherein $R_1$ is selected from the group consisting of H, straight alkyl groups of 1 to 5 carbon atoms, and branched alkyl groups of 3 to 5 carbon atoms, wherein $R_2$ is selected for the group consisting of H, straight alkyl groups of 1 to 4 carbon atoms, branched alkyl groups of 3 or 4 carbon atoms, F, Cl, Br, I, —CF₃, —NO₂, —OR₁, where $R_1$ is as defined hereinabove, —COR₁, where $R_1$ is as defined hereinabove, and —CH₂OH.

2. A compound of formula IA

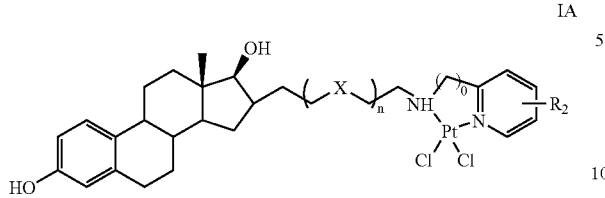

IA wherein X may be —CH$_2$—O—CH$_2$— or —CH$_2$—,
wherein n is 1, 2, 3, 4 or 5 when X is —CH$_2$—O—CH$_2$—, wherein n is 2, 3, 4, 5, 6, 7, 8, 9 or 10 when X is —CH$_2$—, wherein o is 1, 2 or 3, wherein R$_2$ is selected for the group consisting of H, straight alkyl groups of 1 to 4 carbon atoms, branched alkyl groups of 3 or 4 carbon atoms, F, Cl, Br, I, —CF$_3$, —NO$_2$, —OR$_1$, —COR$_1$ and —CH$_2$OH, R$_1$ being selected from the group consisting of H, straight alkyl groups having from 1 to 5 carbon atoms and branched alkyl groups having from 3 to 5 carbon atoms.

3. A compound of formula IB

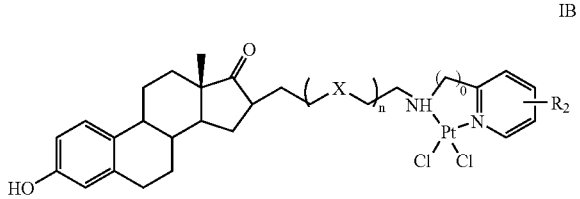

IB wherein X may be —CH$_2$—O—CH$_2$— or —CH$_2$—,
wherein n is 1, 2, 3, 4 or 5 when X is —CH$_2$—O—CH$_2$—, wherein n is 2, 3, 4, 5, 6, 7, 8, 9 or 10 when X is —CH$_2$—, wherein o is 1, 2 or 3, wherein R$_2$ is selected for the group consisting of H, straight alkyl groups of 1 to 4 carbon atoms, branched alkyl groups of 3 or 4 carbon atoms, F, Cl, Br, I, —CF$_3$, —NO$_2$, —OR$_1$, —COR$_1$ and —CH$_2$OH, R$_1$ being selected from the group consisting of H, straight alkyl groups having from 1 to 5 carbon atoms and branched alkyl groups having from 3 to 5 carbon atoms.

4. A compound of formula II

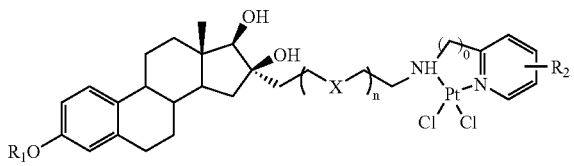

II wherein X may be —CH$_2$—O—CH$_2$— or —CH$_2$—,
wherein n is 1, 2, 3, 4 or 5 when X is —CH$_2$—O—CH$_2$—, wherein n is 2, 3, 4, 5, 6, 7, 8, 9 or 10 when X is —CH$_2$—, wherein o is 1, 2 or 3, wherein R$_1$ is selected from the group consisting of H, straight alkyl groups of 1 to 5 carbon atoms, and branched alkyl groups of 3 to 5 carbon atoms, wherein R$_2$ is selected for the group consisting of H, straight alkyl groups of 1 to 4 carbon atoms, branched alkyl groups of 3 or 4 carbon atoms, F, Cl, Br, I, —CF$_3$, —NO$_2$, —OR$_1$, where R$_1$ is as defined hereinabove, —COR$_1$, where R$_1$ is as defined hereinabove, and —CH$_2$OH.

5. A compound of formula IIA

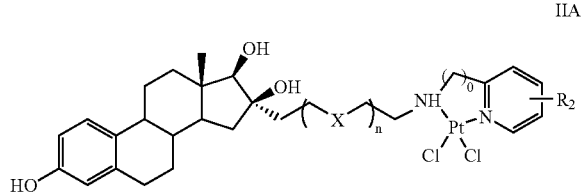

IIA wherein X may be —CH$_2$—O—CH$_2$— or —CH$_2$—,
wherein n is 1, 2, 3, 4 or 5 when X is —CH$_2$—O—CH$_2$—, wherein n is 2, 3, 4, 5, 6, 7, 8, 9 or 10 when X is —CH$_2$—, wherein o is 1, 2 or 3, wherein R$_2$ is selected for the group consisting of H, straight alkyl groups of 1 to 4 carbon atoms, branched alkyl groups of 3 or 4 carbon atoms, F, Cl, Br, I, —CF$_3$, —NO$_2$, —OR$_1$, —COR$_1$ and —CH$_2$OH, R$_1$ being selected from the group consisting of H, straight alkyl groups having from 1 to 5 carbon atoms and branched alkyl groups having from 3 to 5 carbon atoms.

6. A compound as defined in claim 2, wherein X is —CH$_2$—, n is 2, 3, 4, 5, 6, 7, 8, 9 or 10.

7. A compound as defined in claim 5, wherein X is —CH$_2$—, n is 2, 3, 4, 5, 6, 7, 8, 9 or 10.

8. A compound as defined in claim 2, wherein X is —CH$_2$—O—CH$_2$—, n is 1, 2, 3, 4 or 5.

9. A compound as defined in claim 5, wherein X is —CH$_2$—O—CH$_2$—, n is 1, 2, 3, 4 or 5.

10. A compound as defined in claim 2, wherein X is —CH$_2$—, n is 9, o is 1 and R$_2$ is H.

11. A compound as defined in claim 2, wherein X is —CH$_2$—, n is 9, o is 2 and R$_2$ is H.

12. A compound as defined in claim 5, wherein X is —CH$_2$—, n is 2, 4, 6 or 8, o is 1 and R$_2$ is H.

13. A compound as defined in claim 5, wherein X is —CH$_2$—, n is 2, 4, 6 or 8, o is 2 and R$_2$ is H.

14. A compound as defined in claim 5, wherein X is —CH$_2$—O—CH$_2$—, n is 2, o is 2 and R$_2$ is H.

15. A pharmaceutical composition comprising a pharmaceutically acceptable carrier and at least one compound as defined in claim 2.

16. A pharmaceutical composition comprising a pharmaceutically acceptable carrier and at least one compound as defined in claim 5.

17. A pharmaceutical composition comprising a pharmaceutically acceptable carrier and a compound as defined in claim 11.

18. A pharmaceutical composition comprising a pharmaceutically acceptable carrier and at least one compound as defined in claim 13.

19. A pharmaceutical composition comprising a pharmaceutically acceptable carrier and a compound as defined in claim 14.

20. A method for treating a person suffering from breast, uterus or overian cancer which comprises administering to said person a pharmaceutically effective amount of a compound as defined in claim 2.

21. A method for treating a person suffering from breast, uterus or overian cancer which comprises administering to said person a pharmaceutically effective amount of a compound as defined in claim 5.

22. A method for treating a person suffering from breast, uterus or ovarian cancer which comprises administering to said person a pharmaceutically effective amount of a compound as defined in claim 11.

23. A method for treating a person suffering from breast, uterus or ovarian cancer which comprises administering to said person a pharmaceutically effective amount of a compound as defined in claim 13.

24. A method for treating a person suffering from breast, uterus or ovarian cancer which comprises administering to said person a pharmaceutically effective amount of a compound as defined in claim 14.

25. A method for the preparation of a pharmaceutical composition which is useful for treating a person suffering from breast, uterus or ovarian cancer, said method comprising the step of mixing a compound as defined in claim 2 with a pharmaceutically acceptable carrier.

26. A method for the preparation of a pharmaceutical composition which is useful for treating a person suffering from breast, uterus or ovarian cancer, said method comprising the step of mixing a compound as defined in claim 5 with a pharmaceutically acceptable carrier.

27. A method for the preparation of a pharmaceutical composition which is useful for treating a person suffering from breast, uterus or ovarian cancer, said method comprising the step of mixing a compound as defined in claim 11 with a pharmaceutically acceptable carrier.

28. A method for the preparation of a pharmaceutical composition which is useful for treating a person suffering from breast, uterus or ovarian cancer, said method comprising the step of mixing a compound as defined in claim 13 with a pharmaceutically acceptable carrier.

29. A method for the preparation of a pharmaceutical composition which is useful for treating a person suffering from breast, uterus or ovarian cancer, said method comprising the step of mixing a compound as defined in claim 14 with a pharmaceutically acceptable carrier.

* * * * *

UNITED STATES PATENT AND TRADEMARK OFFICE
CERTIFICATE OF CORRECTION

PATENT NO. : 7,153,844 B2  Page 1 of 2
APPLICATION NO. : 10/397332
DATED : December 26, 2006
INVENTOR(S) : Gervais Bérubé

It is certified that error appears in the above-identified patent and that said Letters Patent is hereby corrected as shown below:

Title page item [57] in the abstract, the expression "where $R_1$ is as defined hereinabove, -$COR_1$, where $R_1$ is as defined hereinabove, and –$CH_2OH$" should read -- -$COR_1$ and –$CH_2OH$, where $R_1$ is as defined hereinabove --.

Column 4, line 41, the formula II should appear as follows:

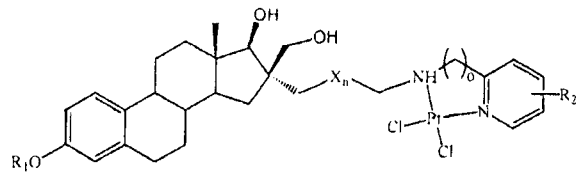

II

Column 5, line 1, the formula IIA should appear as follows:

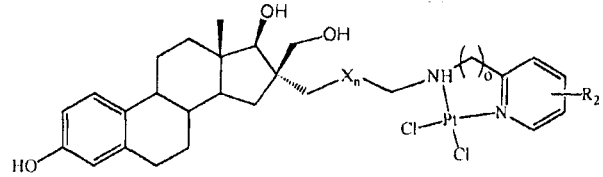

IIA

Column 44, line 40, claim 1 the formula I should appear as follows:

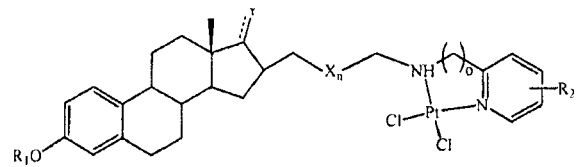

I

Signed and Sealed this

Twenty-fifth Day of May, 2010

David J. Kappos
*Director of the United States Patent and Trademark Office*

Column 45, line 2, claim 2 the formula IA should appear as follows:
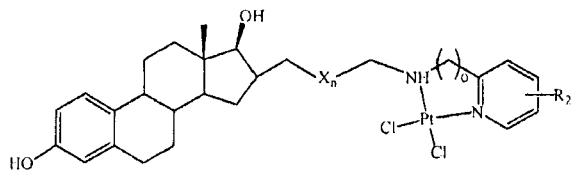
IA
Column 45, line 25, claim 3 the formula IB should appear as follows:
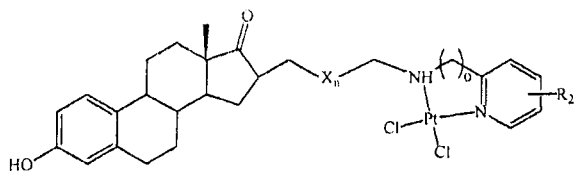
IB       ;
line 48, the formula II should appear as follows:
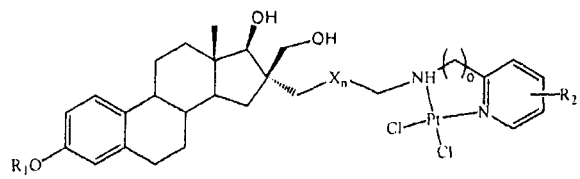
II
Column 46, line 6, claim 5 the formula IIA should appear as follows:
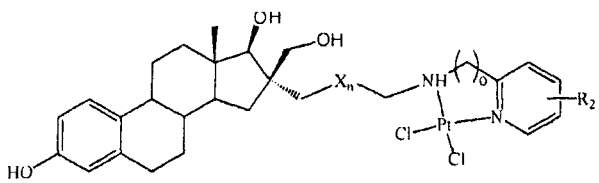
IIA